(12) United States Patent
Kasahara et al.

(10) Patent No.: US 7,198,754 B2
(45) Date of Patent: Apr. 3, 2007

(54) BIOLOGICAL MATERIAL DETECTION ELEMENT, BIOLOGICAL MATERIAL DETECTION METHOD AND APPARATUS, CHARGED MATERIAL MOVING APPARATUS

(75) Inventors: Akihiro Kasahara, Sambu-gun (JP); Yoshio Ishimori, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 581 days.

(21) Appl. No.: 10/230,149

(22) Filed: Aug. 29, 2002

(65) Prior Publication Data
US 2003/0044997 A1 Mar. 6, 2003

(30) Foreign Application Priority Data
Aug. 31, 2001 (JP) ............................. 2001-264696
Aug. 31, 2001 (JP) ............................. 2001-264716
Aug. 31, 2001 (JP) ............................. 2001-264752

(51) Int. Cl.
*G01N 15/06* (2006.01)
*G01N 33/00* (2006.01)
*G01N 33/48* (2006.01)
*C12Q 1/68* (2006.01)
*B32B 5/02* (2006.01)

(52) U.S. Cl. ..................... 422/82.01; 422/50; 422/68.1; 422/81; 422/82; 422/82.02; 436/43; 436/52; 436/53; 436/63; 436/149; 204/193; 204/194; 204/400; 204/403.01; 204/406; 204/409; 204/411; 204/164; 204/450; 204/461

(58) Field of Classification Search ............... 422/50, 422/68.1, 81, 82, 82.01, 82.02; 436/43, 52, 436/53, 63, 149; 204/193, 194, 400, 403.01, 204/406, 409, 411, 164, 450, 461
See application file for complete search history.

(56) References Cited

U.S. PATENT DOCUMENTS

| 4,959,134 | A | * | 9/1990 | Gross et al. ................. 204/461 |
| 6,068,818 | A | | 5/2000 | Ackley et al. |
| 6,467,630 | B1 | * | 10/2002 | Zborowski et al. ......... 209/459 |
| 6,858,184 | B2 | * | 2/2005 | Pelrine et al. ............. 422/68.1 |

FOREIGN PATENT DOCUMENTS

| CN | 1284082 A | 2/2001 |
| JP | 8-327597 | 12/1996 |
| JP | 9-15122 | 1/1997 |
| JP | 9-503307 | 3/1997 |
| JP | 2001-50931 | 2/2001 |
| WO | WO 95/12808 | 5/1995 |
| WO | WO 96/07917 | 3/1996 |
| WO | WO 99/42558 | 8/1999 |
| WO | WO 01/35100 | 5/2001 |

* cited by examiner

*Primary Examiner*—Brian Sines
(74) *Attorney, Agent, or Firm*—Oblon, Spivak, McClelland, Maier & Neustadt, P.C.

(57) ABSTRACT

A biological material detection apparatus which detects a charged biological material such as a gene or protein contained in a sample liquid is disclosed. A biological material detection element includes a substrate, at least one first electrode formed on the substrate, and a plurality of second electrodes which are arrayed at predetermined intervals around the first electrode on the substrate along the circumferential direction and to which ligands that react with predetermined biological materials are respectively immobilized. A sample liquid is introduced toward the first electrode on the substrate. The introduced sample liquid is moved radially toward the second electrodes by electrical control.

4 Claims, 17 Drawing Sheets

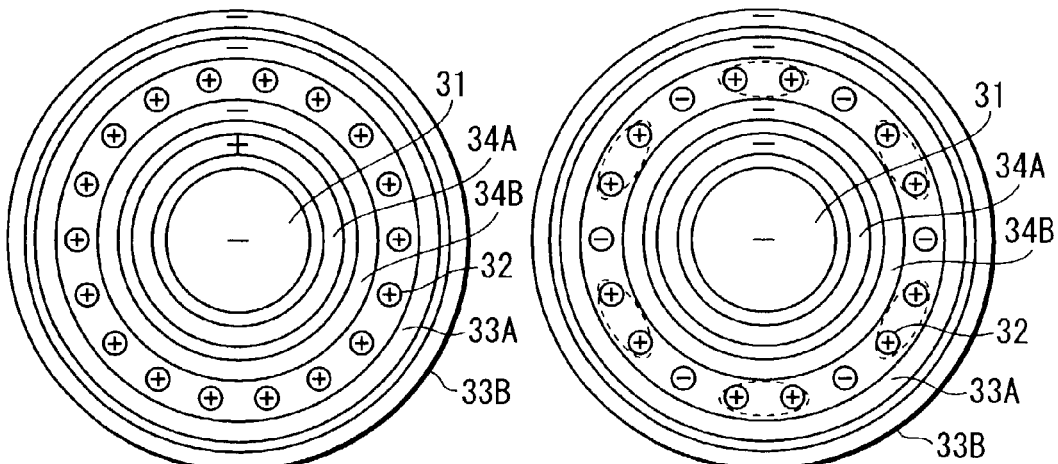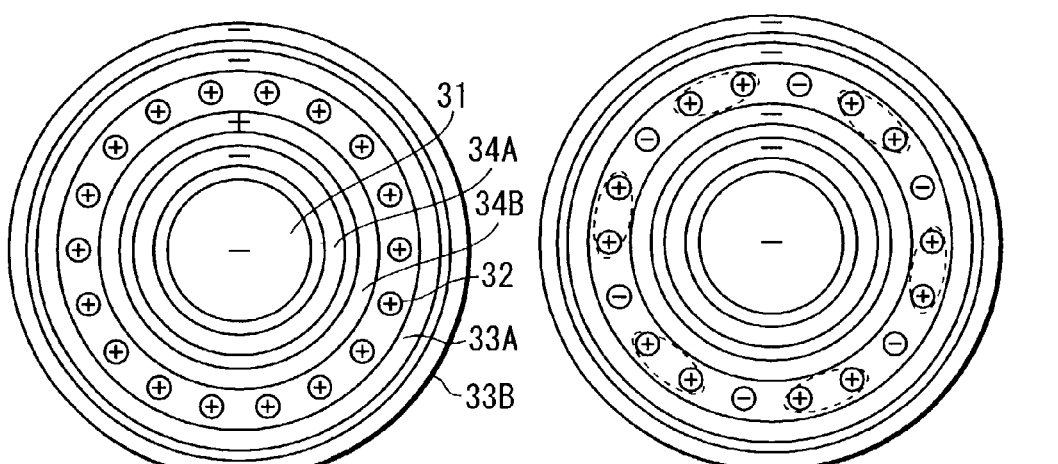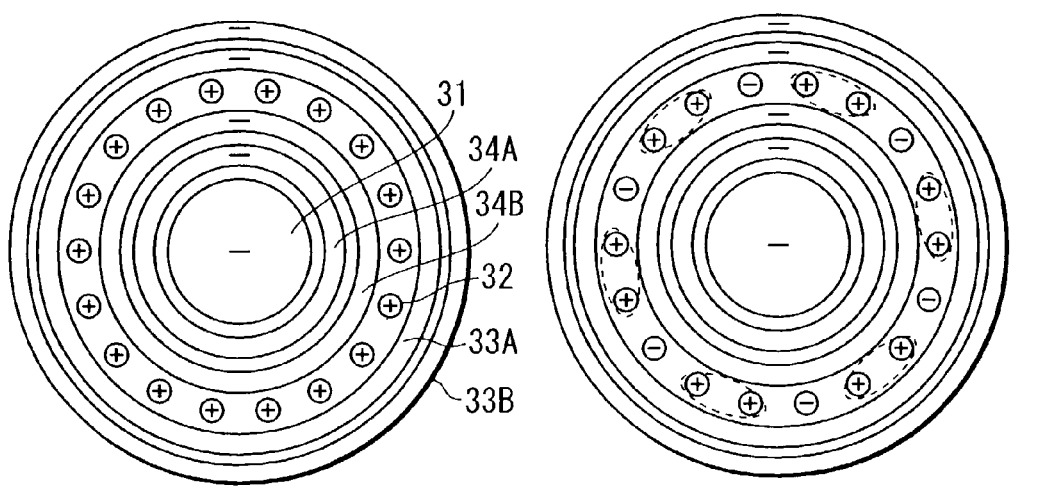
FIG. 7A    FIG. 8A
FIG. 7B    FIG. 8B
FIG. 7C    FIG. 8C

BIOLOGICAL MATERIAL DETECTION ELEMENT, BIOLOGICAL MATERIAL DETECTION METHOD AND APPARATUS, CHARGED MATERIAL MOVING APPARATUS

CROSS-REFERENCE TO RELATED APPLICATIONS

This application is based upon and claims the benefit of priority from the prior Japanese Patent Applications No. 2001-264696, filed Aug. 31, 2001; No. 2001-264716, filed Aug. 31, 2001; and No. 2001-264752, filed Aug. 31, 2001, the entire contents of all of which are incorporated herein by reference.

BACKGROUND OF THE INVENTION

1. Field of the Invention

The present invention relates to a biological material detection element, biological material detection method and apparatus, and charged material moving apparatus which are used to detect biological materials such as genes and proteins.

2. Description of the Related Art

Recently, systems for detecting biological materials such as genes and proteins have been under development. For example, the detection of genes is used for the prediction of the curative effect produced by interferon. A conventional biological material detection technique will be described with reference to an example of the prediction of curative effect produced by interferon.

It is known that when a person is infected with hepatitis C, this disease is likely to proceed to hepatic cancer through hepatic hepatocirrhosis. One of the medical treatments for the disease is a method using interferon. It is reported that the injection of interferon has a curative effect on only about 20 to 30% of the Japanese, and causes strong side effects even if it produces the curative effect. For this reason, attention has recently begun to be paid to personalized medical treatment in which the curative effect of interferon is predicted, and interferon is used only when a curative effect can be expected.

As a method of predicting the curative effect of interferon, a method of checking the type of virus and the amount of virus at the gene level is known. It is thought that interferon has little effect on type $1b$ with which many Japanese are infected, but does have a curative effect on type $2a$, and that interferon has little effect when the amount of virus is $10^6$ copy/mL or more. In actual diagnoses, these factors are often mixed, resulting in difficulty in prediction. Recently, as a method of predicting the curative effect of interferon, a method has been reported, in which single nucleotide polymorphism (SNP) that exists in the promoter region of gene that codes for MxA protein is used as a marker. According to this report, if the SNP is of type G/G, the effect of interferon is small, whereas if the SNP is of type G/T or T/T, interferon works effectively.

As described above, it is becoming possible to predict the curative effect of interferon by analysis at the gene level. All these methods have used cumbersome, expensive conventional techniques (electrophoresis, Microplate EIA, and the like), and hence more simplified methods have been required for clinical examination.

Under the circumstances, attention has recently been paid to a gene inspection technique using a biological material detection element called a DNA chip (Beattie et al. 1993, Fodor et al. 1991, Khrapko et al. 1989, and Southern et al. 1994). The DNA chip is formed from a several cm square glass or silicon chip on which a plurality of types of DNA probes with different sequences are immobilized. A mixture of a sample gene marked by a fluorescent dye, radiation isotopic element (RI), or the like or non-marked sample gene and marked oligonucleotide is caused to react on the chip. If there is a sequence, in the sample, which is complementary to a DNA probe on the chip, a signal originating from the marker can be obtained at a specific portion on the chip. If the sequences and position of the immobilized DNA probes are known in advance, a base sequence existing in the sample gene can be easily checked. Such a DNA chip makes it possible to obtain many kinds of information concerning base sequences by one test, and hence can be used for a clinical diagnosis technique (Pease et al. 1994, Parinov et al. 1996).

The principle of an electrochemical gene detection method using a DNA chip is schematically shown in FIG. 25.

In a typical conventional DNA chip, a sample liquid made of an aqueous solution of genes is introduced from a sample liquid introduction portion placed on one end portion of the chip surface, flows on various DNA probes immobilized in the cells of a matrix, and then is discharged from a sample liquid discharge portion placed on the other end portion of the chip surface. The overall DNA chip is covered with a resin case, and the portion where the DNA probes are immobilized is made transparent to read optical signals such as fluorescence.

The above conventional DNA chip is designed such that in the process in which a sample liquid flows from one end portion of the chip surface to the other end portion, the liquid is guided on the DNA probes arrayed in the form of a matrix. Since it is difficult to make the sample liquid uniformly flow on the DNA probes, it is difficult to make the gene and a DNA probe reliably react with each other. This tends to cause variations in detection result.

In addition, in general, since the gene concentration in a sample liquid is low, when a conventional DNA chip has no gene concentrating effect, in particular, a gene to be detected must be amplified in advance by a gene amplification method such as the PCR method.

Conventionally, in a biological material detection apparatus for detecting genes by electrochemical measurement using a DNA chip, current measurement is performed while a voltage is applied between electrodes in a proper electrolytic solution stored in a vessel 100, as shown in FIG. 27. Electrodes 101, 102, and 103 called a counterelectrode, reference electrode, and working electrode, are inserted in the vessel 100.

The reference electrode 102 is an electrode for applying a reference potential to the counterelectrode 101, which is held at a predetermined potential. A voltmeter 106 is connected between the counterelectrode 101 and the reference electrode 102 to measure the potential of the counterelectrode 101. Besides, a variable DC voltage source 104 is connected between the counterelectrode 101 and the working electrode 103. The variable DC voltage source 104 varies an applied voltage between the counterelectrode 101 and the working electrode 103. The voltage sweeping causes a current change, which is measured by an ammeter 105, thus detecting a gene.

FIG. 28 shows a procedure for detecting a gene by biological material detection apparatus having an arrangement like that shown in FIG. 27 using a nucleic acid intercalating agent. First of all, a sample liquid is supplied (step S1). With this operation, the sample liquid is made to adhere to a DNA probe (single stranded DNA that reacts with a specific gene) immobilized to the working electrode to convert the DNA in the liquid into a single stranded DNA, thus performing hybridization. The sample liquid that did not adhere the DNA probe is then cleaned (step S2). Subsequently, an intercalating reagent (nucleic acid intercalating agent) that reacts specifically with a double stranded DNA is supplied to improve the detection sensitivity (step S3), and the unnecessary intercalating agent is further cleaned (step S4). Finally, a voltage is applied between the counterelectrode 101 and the working electrode 103, and an oxidation current obtained from the intercalating agent is measured, i.e., an electrochemical signal obtained from the intercalating agent is measured (step S5).

A current-potential curve of Hoechst 33258 as a DNA binder is shown in FIG. 26.

As described above, in the conventional biological material detection apparatus, since current measurement can be performed only once with respect to one working electrode (DNA chip), it is difficult to improve the gene detection sensitivity. FIG. 29 shows a change in current density when a given plasmid (pYRB259) is measured by using an electrochemical DNA chip. As is obvious, since the background current is high, a low-concentration gene cannot be detected. In general, since the gene concentration of a sample liquid is low, a target gene must be amplified in advance by a gene amplification method such as the PCR method.

BRIEF SUMMARY OF THE INVENTION

The present invention has as its object to provide a biological material detection element and detection apparatus which can make a detection target biological material and a ligand reach with each other under a uniform condition.

It is another object of the present invention to concentrate a biological material in a sample liquid during detection.

In order to achieve the above objects, according to embodiments of the present invention, there is provided a biological material detection element which introduces a sample liquid containing a charged biological material and detects the biological material, comprising: a substrate; at least one first electrode placed at a position on the substrate to which the sample liquid is introduced; and a plurality of second electrodes which are arrayed at predetermined intervals around the first electrode on the substrate in a circumferential direction and to which ligands that react predetermined biological materials are respectively immobilized.

According to embodiments of the present invention, there is provided a biological material detection apparatus which detects a charged biological material contained in a sample liquid, comprising: a biological material detection element having a substrate and a plurality of electrodes which are arrayed at predetermined intervals along a circumferential direction on the substrate and to which ligands that react predetermined biological materials are respectively immobilized; a sample liquid introduction part to introduce the sample liquid to a central portion of the array of the electrodes on the substrate; and a sample liquid moving mechanism to move the sample liquid introduced to the central portion on the substrate by the sample liquid introduction part radially toward the electrodes.

According to embodiments of the present invention, there is provided a biological material detection method of detecting a charged biological material contained in a sample liquid with a biological material detection element formed by arraying, on a substrate, electrodes to which ligands that react with predetermined biological materials are respectively immobilized, the method comprising: after supplying the sample liquid onto the biological material detection element, repeating a series of steps of (a) supplying an intercalating agent onto the biological material detection element, (b) measuring an electrochemical signal from the intercalating agent which is based on a reaction between the charged biological material and the ligand, and (c) removing the intercalating agent adhering to the ligand, thereby detecting the charged biological material.

According to embodiments of the present invention, there is provided a charged material moving apparatus which moves a charged material having a specific charge polarity, comprising: a substrate; a plurality of electrodes arrayed on the substrate along a specific direction; and a driving circuit which moves the charged material onto the plurality of electrodes along the specific direction by performing driving operation of applying a voltage having an opposite polarity to the charge polarity of the charged material to some of the plurality of electrodes while sequentially changing a position of an electrode to which the voltage having the opposite polarity is to be applied.

BRIEF DESCRIPTION OF THE SEVERAL VIEWS OF THE DRAWING

FIGS. 7A to 7C are views for explaining the electrode arrangement of a biological material detection element according to a modification of the first embodiment and the concentration of a detection target biological material and its movement to a peripheral portion in the biological material detection element;

FIGS. 8A to 8C are views for explaining the movement of a detection target biological material on working electrodes in the biological material detection element according to another modification of the first embodiment;

DETAILED DESCRIPTION OF THE INVENTION

The embodiments of the present invention will be described below with reference to the views of the accompanying drawing.

FIRST EMBODIMENT

Figure 1:
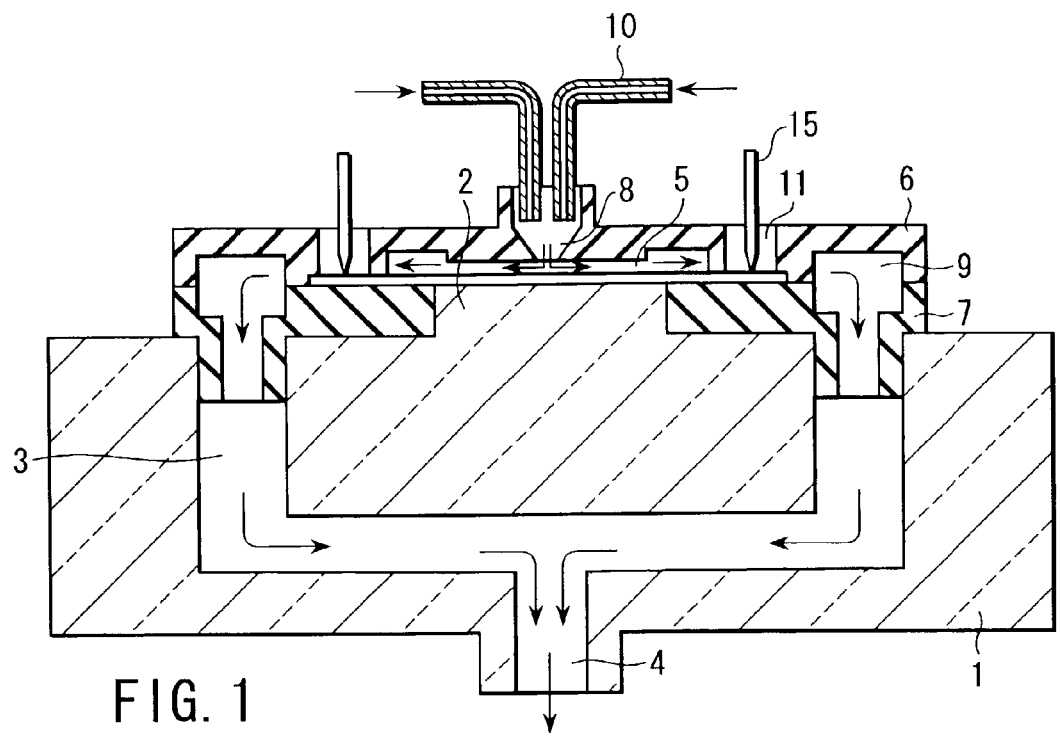
FIG. 1 is a sectional view showing the arrangement of a biological material detection apparatus including a biological material detection element according to a first embodiment of the present invention.

FIG. 1 is a sectional view showing the arrangement of a biological material detection apparatus including a biological material detection element according to a first embodiment of the present invention. A base 1 has a protruding element mount portion 2 on its central upper portion on which a biological material detection element 5 (to be described in detail later) is mounted. The base 1 also has a sample liquid passage hole 3 in the two sides in FIG. 1 and a sample liquid outlet 4 in a central lower portion which communicates with the sample liquid passage hole 3.

An upper holder 6 and lower holder 7 are mounted on the base 1. The upper and lower holders hold the biological material detection element 5 mounted on the element mount portion 2 from both upper and lower sides, and mainly guide a sample liquid into the element 5 and the sample liquid passing through the element 5 into the sample liquid passage hole 3. The structures of the upper and lower holders 6 and 7 will be described in detail later.

A sample liquid introduction portion 8 is formed in the central portion of the upper holder 6. The distal end of a sample liquid supply pipe 10 is connected to this sample liquid introduction portion 8. A sample liquid source (not shown) is connected to the proximal end portion (not shown) of the sample liquid supply pipe 10. A sample liquid receiving a proper positive pressure is introduced from this sample liquid source into the sample liquid introduction portion 8. The sample liquid introduced into the sample liquid introduction portion 8 is guided onto the biological material detection element 5 and used for the detection of a biological material. Thereafter, the sample liquid is discharged outside from a sample liquid outlet 4, under a proper negative pressure, through a sample liquid guide duct 9 formed by the lower and upper holders 6 and 7 and the sample liquid passage hole 3 formed in the base 1.

A rectangular through hole 11 is formed in the upper holder 6. The distal end of a contact electrode 15 can be brought into contact with an electrode serving as a working electrode on the biological material detection element 5 by inserting the contact electrode 15 via the through hole 11. By using this contact electrode 15, a biological material detection signal can be extracted as an electrical signal such as a current or potential signal.

Figure 2A:
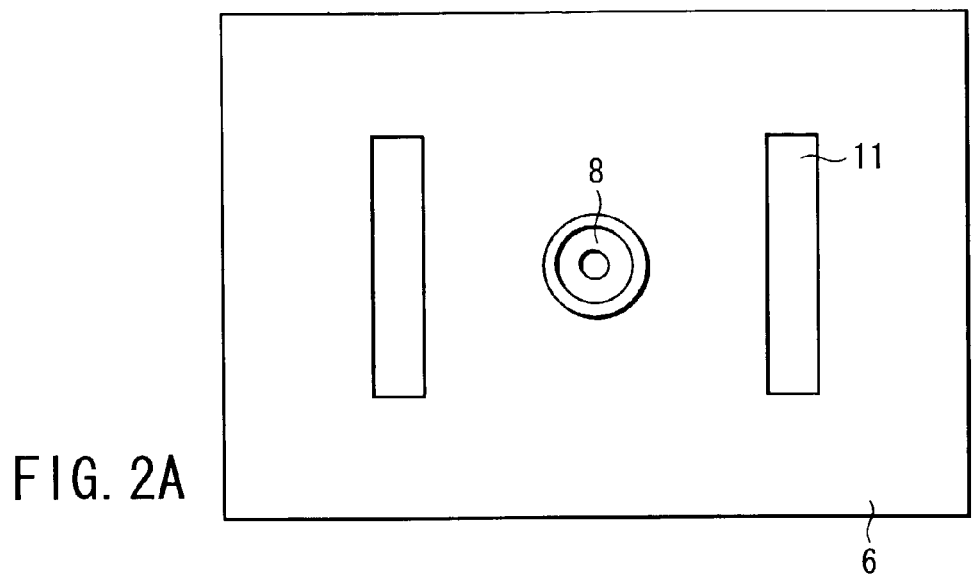
FIG. 2A is a plan view of an upper holder in the first embodiment.
Figure 2B:
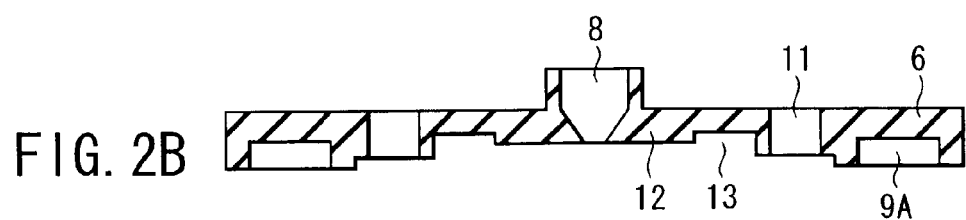
FIG. 2B is a sectional view of the upper holder in the first embodiment.
Figure 2C:
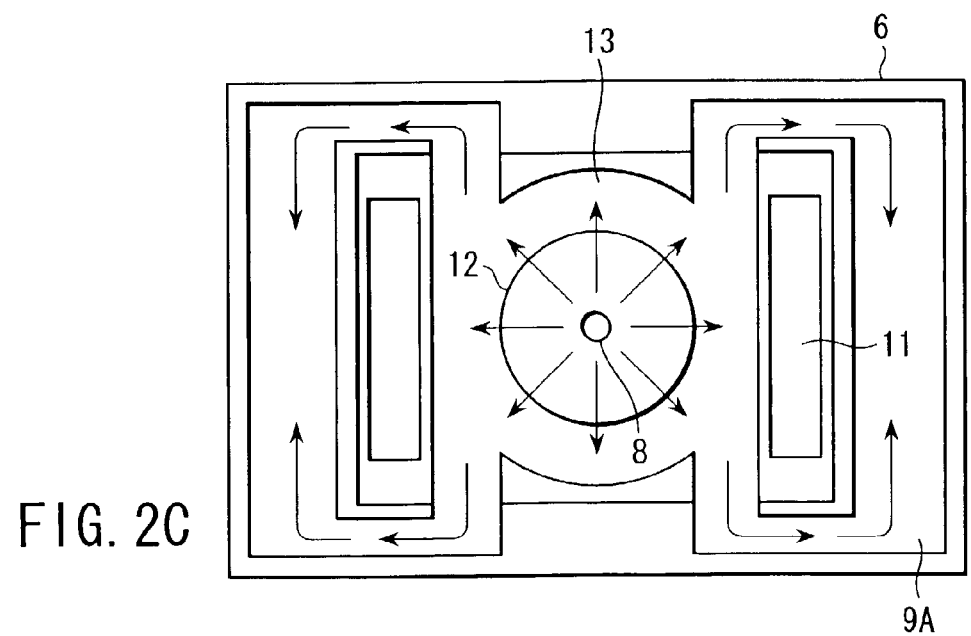
FIG. 2C is a bottom view of the upper holder in the first embodiment.

FIGS. 2A, 2B, and 2C are a plan view, sectional view, and bottom view of the upper holder 6, respectively. Referring to FIG. 2C, the passageways of a sample liquid are indicated by the arrows in FIG. 2C. A central portion 12 (a portion of the base 1 which opposes the element mount portion 2) on the lower surface of the upper holder 6 which opposes the biological material detection element 5 slightly protrudes downward. A ring-like sample liquid passage hole 13 communicating with the sample liquid guide duct 9 shown in FIG. 1 is formed around the central portion 12. A recess portion 9A that forms the sample liquid guide duct 9 is formed in the lower surface of the upper holder 6.

The sample liquid introduction portion 8 formed in the central portion of the upper holder 6 is a tapered hole. The sample liquid introduced into this sample liquid introduction portion 8 spreads radially. In this process, the sample liquid is guided onto a ligand immobilizing portion of the biological material detection element 5. Subsequently, the sample liquid is guided to the sample liquid guide duct 9 through the sample liquid passage hole 13 and discharged outside from the sample liquid outlet 4 through the sample liquid passage hole 3 formed in the base 1, as described above.

Figure 3A:
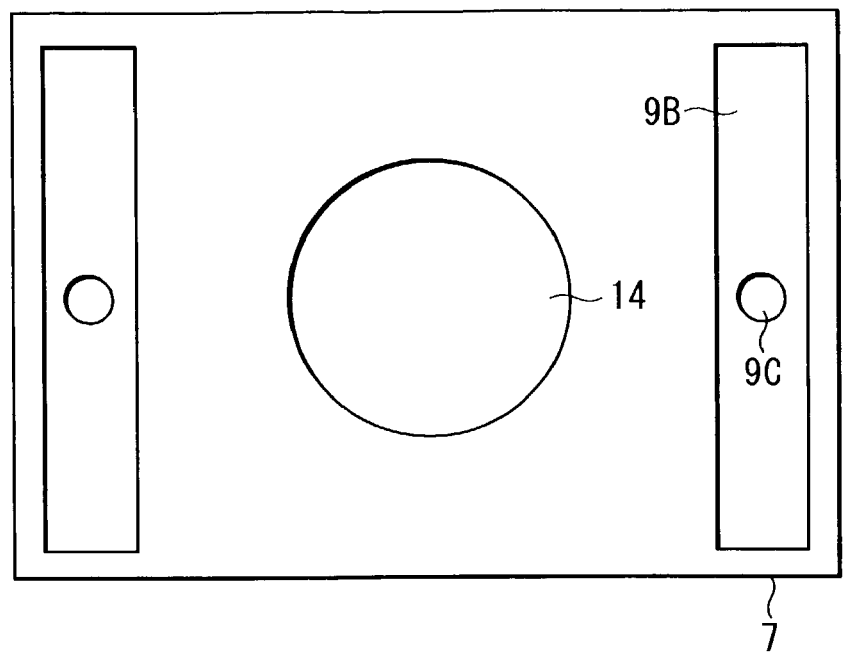
FIG. 3A is a plan view of a lower holder in the first embodiment.
Figure 3B:
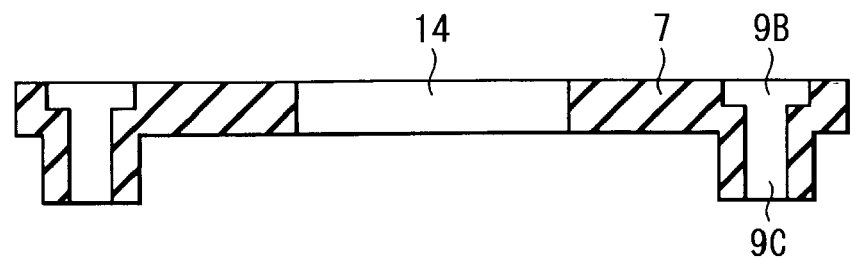
FIG. 3B is a sectional view of the lower holder in the first embodiment.
Figure 3C:
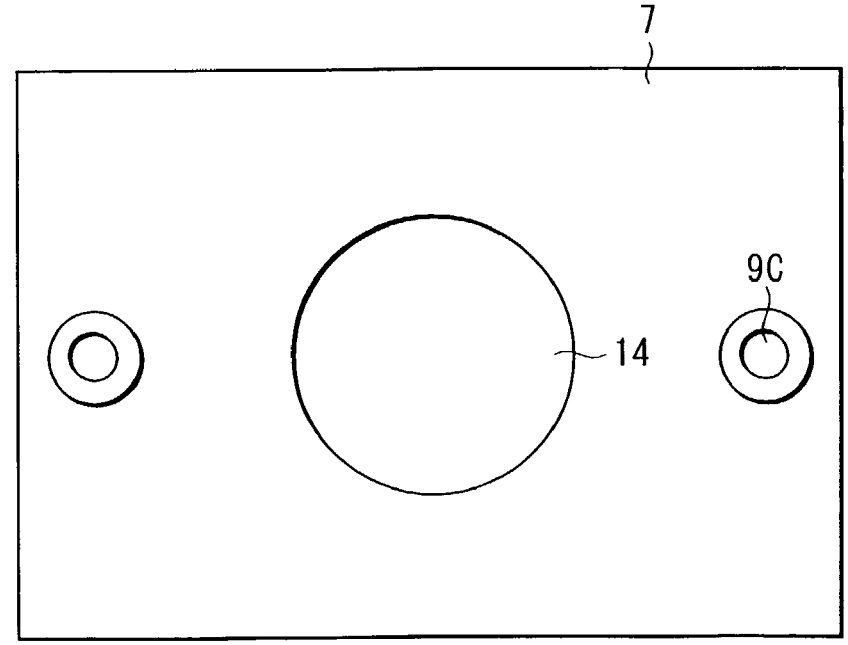
FIG. 3C is a bottom view of the lower holder in the first embodiment.

FIGS. 3A, 3B, and 3C are a plan view, sectional view, and bottom view of the lower holder 7, respectively. The lower holder 7 has a hole 14 in its central portion, in which the element mount portion 2 of the base 1 shown in FIG. 1 is inserted. Rectangular recess portions 9B and circular holes 9C communicating with the recess portions 9B, which partly form the other portion of the sample liquid guide duct 9 shown in FIG. 1, are formed in both the left and right sides of the lower holder 7 in FIGS. 3A to 3C.

The sample liquid supplied from the sample liquid supply pipe 10 in this manner is guided by the upper holder 6 and lower holder 7 and introduced from the central portion into the biological material detection element 5. After the sample liquid is uniformly supplied to the ligand immobilizing portions formed on the peripheral portion of the element 5, the liquid is discharged from below. Detection of a biological material in the sample liquid can therefore be done under a uniform condition.

As shown in FIG. 1, the biological material detection element 5 is held by the upper holder 6 and lower holder 7. In this case, the biological material detection element 5 may be immobilized to the biological material detection apparatus, i.e., may have an electrode-integrated arrangement. Alternatively, the element 5 may be designed to be detached from the biological material detection apparatus by detaching the upper holder 6, i.e., may have an electrode separation type arrangement.

The detailed arrangement of the biological material detection element 5 according to this embodiment will be described next with reference to FIG. 4.

Figure 4:
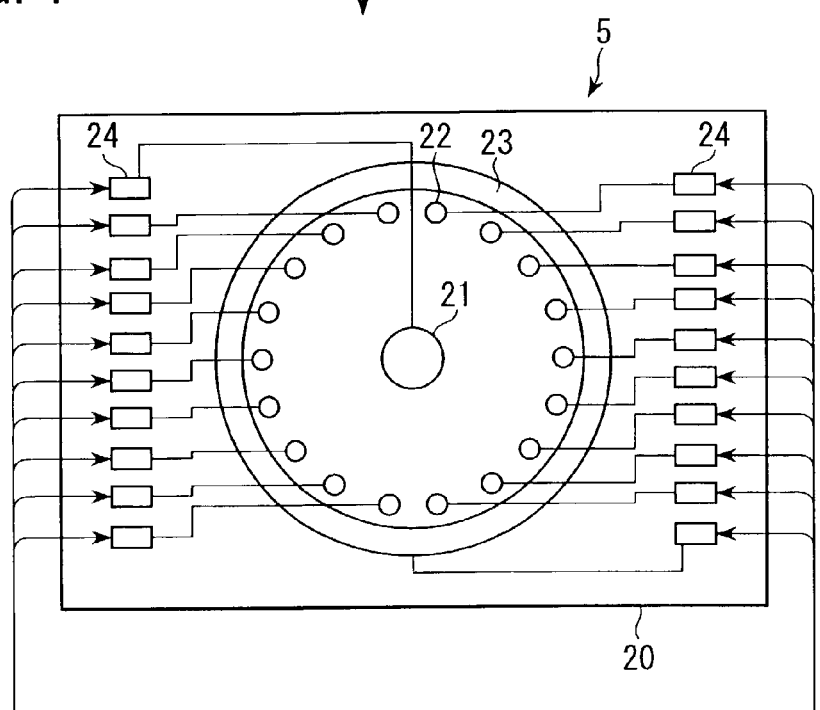
FIG. 4 is a plan view of the biological material detection element according to the first embodiment, showing how a driving circuit is connected to the biological material detection element.

As shown in FIG. 4, the biological material detection element 5 is formed by forming electrodes 21, 22, and 23 and electrode pads 24 on an element substrate 20. The surfaces of the electrodes 21, 22, and 23 may be flush with the surface of the element substrate 20, or may be embedded to be slightly recessed from the surface of the element substrate 20. The electrodes 21, 22, and 23 and electrode pads 24 are connected to each other through, for example, a multilayer interconnection formed on the element substrate 20.

The circular electrode 21 formed on the central portion functions as a counterelectrode. The electrode 23 formed in an annular shape centered on the electrode 21 functions as a reference electrode for providing a reference potential for the counterelectrode. The circular electrodes 22 are arranged at a predetermined pitch on a circumference on the inner side of the electrode 23. These electrodes 22 function as working electrodes for detecting a biological material. The surfaces of the electrodes 21, 22, and 23 are covered with a thin insulating film (not shown), and this thin insulating film is subjected to lithography processing. In the lithography processing, parts of the surfaces of the electrode 21 and 23 are removed, and the conductive portions of the electrodes are exposed so that electrical signals can be taken out through the parts. The details of the lithography processing carried out on the thin insulating film will be described later.

At least one specific detection ligand is immobilized to the electrode 22 serving as a working electrode. That is, electrode 22 also serves as a ligand immobilizing portion. The ligand immobilized to each electrode 22 is selected from one of, for example, a gene, gene probe, protein, protein segment, coenzyme, receptor, and sugar chain in accordance with the biological material to be detected.

If different ligands are immobilized to the respective electrodes 22, a plurality of biological materials can be detected at once. In addition, if identical ligands are immobilized to the respective electrodes 22, many biological materials can be detected at once. If many electrodes 22 (ligand immobilizing portions) are patterned on the element substrate 20 in advance by photolithography, the productivity of biological material detection elements 5 improves.

If a biological material to be detected is a gene, a DNA probe is immobilized as a ligand to the electrode 22. As is known, a DNA probe is a single stranded gene that reacts with a specific gene. If genes in a sample liquid are converted into a single stranded gene in advance, only a gene having a specific sequence in correspondence with the DNA probe immobilized to the electrode 22 is trapped by the electrode 22. Subsequently, the DNA probe and the gene are complementarily bound to each other (hybridization).

The above arrangement will be described in further detail. First of all, a substrate material used for the element substrate 20 is, but is not limited to, an inorganic insulating material such as glass, silica glass, alumina, sapphire, forsterite, silicon carbide, silicon oxide, or silicon nitride, for example. Alternatively, one of the following organic materials can be used as a substrate material: polyethylene, ethylene, polypropylene, polyisobutylene, polymethylmethacrylate, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, a styrene-acrylonitrile copolymer, an acrylonitrile-butadiene-styrene copolymer, silicone resin, polyphenylene oxide, polysulfone, and the like. In addition, if biological material detection is to be performed by the optical method to be described later, a thin fiber film such as nylon or cellulose can be used.

The electrode materials to be used for the electrodes 21, 22, and 23 are not specifically limited. As a material (including ligand immobilizing spot) for the electrode 22 serving as a working electrode, in particular, when biological material detection is to be performed electrochemically, one of the following materials can be used: a single metal such as gold, gold alloy, silver, platinum, mercury, nickel, palladium, silicon, germanium, gallium, or tungsten, alloys each containing at least two of these metals, carbon such as graphite or glassy carbon, oxides thereof, compounds thereof, semiconductor compounds such as silicon oxide, and various kinds of semiconductor devices such as a CCD, FET, and CMOS, for example.

As a method of forming the electrodes 21, 22, and 23, plating, printing, sputtering, vapor deposition, or the like can be used. As a vapor deposition method, one of a resistance-heating method, RF heating method, and electron beam heating method can be used. As a sputtering method, one of DC bipolar sputtering, bias sputtering, asymmetrical AC sputtering, getter sputtering, and RF sputtering can be used. For an electrode, an electrolytic polymer film or conductive high polymer such as polypyrrole or polyaniline can be used.

An insulating material used for a thin insulating film that covers the surfaces of the electrodes 21, 22, and 23 is, but is not limited to, photopolymer or photoresist material, for example. As a photoresist material, an exposure photoresist, far ultraviolet photoresist, X-ray photoresist, or electron beam photoresist may be used. A main material for an exposure photoresist includes cyclized rubber, polycinnamic acid, and novolac resin. As a far ultraviolet photoresist, cyclized rubber, phenol resin, polymethylisopropenylketone (PMIPK), polymethylmethacrylate (PMMA), or the like may be used. As an X-ray photoresist, a material written in "Thin Film Handbook" (Ohmsha, Ltd.) as well as a COP and metal acrylate. As an electron beam resist, a material written in "Thin Film Handbook" (Ohmsha, Ltd.) such as PMMA can be used. The resist to be used in this case preferably has a thickness of 10 nm or more and 1 mm or less.

The area of the electrode 22 serving as a working electrode can be made uniform by covering the electrode 22 with a photoresist and performing lithography. With this process, the amounts of ligand such as DNA probe to be immobilized become uniform among the electrodes 22. This makes it possible to perform biological material detection with excellent reproducibility. Conventionally, a resist material is generally removed in the end. If, however, the electrode 22 is used for the detection of a gene immobilized to a DNA probe, the resist material can be used as part of the electrode 22 without being removed. In this case, a material having high water resistance must be used as a resist material.

For the thin insulating film to be formed on the electrodes 21, 22, and 23, a material other than photoresist materials can be used. For example, oxides, nitrides, and carbides of Si, Ti, Al, Zn, Pb, Cd, W, Mo, Cr, Ta, Ni, and the like and alloys thereof can be used. After a thin film is formed by sputtering, vapor deposition, CVD, or the like using one of these materials, the film is patterned by photolithography to form exposed electrode portions, thus controlling the area constant.

These electrodes 21, 22, and 23 are connected to a driving circuit 25 via the electrode pads 24. The driving circuit 25 applies voltages with predetermined polarities to the respective electrodes 21, 22, and 23 to disperse the sample liquid, introduced onto the central portion on the biological material detection element 5, to the surroundings radially, guide the liquid onto a given electrode 22 serving as a working electrode, and sequentially move a detection target biological material in the sample liquid on the electrode 22 in the array direction (circumferential direction) of the electrodes 22.

This operation will be described below with reference to FIGS. 5A to 5C. When a detection target biological material is a gene, a sample liquid which is an aqueous solution of genes is introduced from the sample liquid supply pipe 10 onto the biological material detection element 5 via the sample liquid introduction portion 8 and supplied onto the electrode 21 on the central portion. The charge polarity of the gene is negative.

Figure 5A:
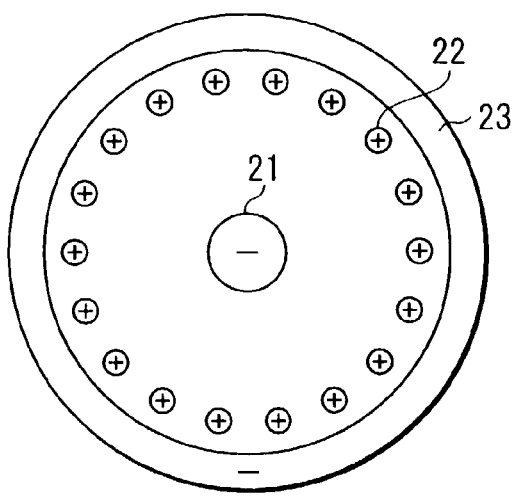
FIGS. 5A to 5C are views for explaining the basic operation of the biological material detection element according to the first embodiment.

As shown in FIG. 5A, when the sample liquid is to be introduced, the driving circuit 25 applies a negative voltage whose polarity is the same as the charge polarity of the gene to the electrode 21 serving as a counterelectrode, a positive voltage whose polarity is opposite to the charge polarity of the gene to the electrodes 22 serving as working electrodes, and a negative voltage to the electrode 23 as a reference electrode. The sample liquid supplied onto the electrode 21 receives electrostatic repulsive force from the electrode 21 to which the negative voltage whose polarity is the same as the charge polarity of the gene is applied, and moves radially toward the peripheral portion. In this case, when a slight negative pressure is applied to the sample liquid, the sample liquid moves more quickly.

The sample liquid that has moved from the electrode 21 toward the peripheral portion will reach the electrode 22. In this case, since a positive voltage whose polarity is opposite to the charge polarity of the genes in the sample liquid is applied, the gene is trapped on the electrode 22 by electrostatic attracting force. In this case, since a negative voltage whose polarity is the same as the charge polarity of the gene is applied to the ring-like electrode 23 serving as a reference electrode placed on the outer circumferential side of the electrodes 22, like the electrode 21, the gene on the electrode 22 receives electrostatic attracting force originating from the electrode 23 to be confined and does not move outside from the electrode 23.

When a gene in the sample liquid is trapped on the electrode 22 in this manner, the DNA probe which is the ligand immobilized to the electrode 22 and the specific gene in the sample liquid react and bind with each other. This is hybridization. In this case, the gene on the electrode 22 is concentrated when it is confined by electrostatic attracting force originating from the electrode 23, as described above, and hence the gene efficiently reacts with the ligand, i.e., hybridization is efficiently performed.

Figure 5B:
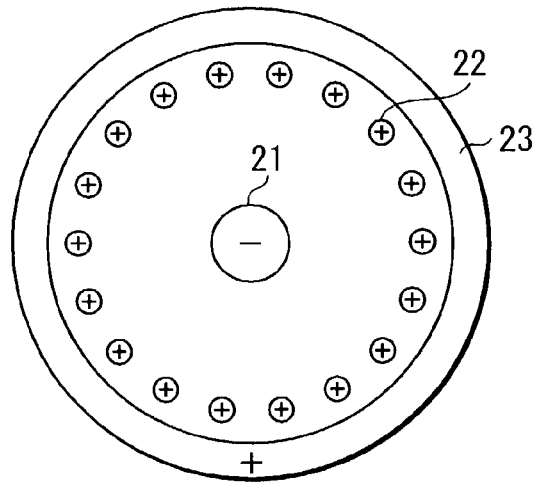

As shown in FIG. 5B, the polarity of only the voltage applied to the electrode 23 is changed to positive polarity which is opposite to the charge polarity of the gene while the polarities of the voltages applied to the electrodes 21 and 22 are kept the same as those shown in FIG. 5A. With this operation, of the genes in the sample liquid on the electrode 22, genes that did not contribute to reaction with the ligand are separated from the electrode 22 by the electrostatic attracting force originating from the electrode 23 and trapped on the electrode 23.

When voltages with negative polarity are applied to both the electrode 22 and the electrode 23, the genes that have been trapped on the electrode 23, i.e., that have not contributed to reaction with the ligand, are further moved outward and discharged from the sample liquid outlet 4, together with the sample liquid on the element substrate 20, via the sample liquid guide duct 9 and sample liquid passage hole 3

Figure 5C:
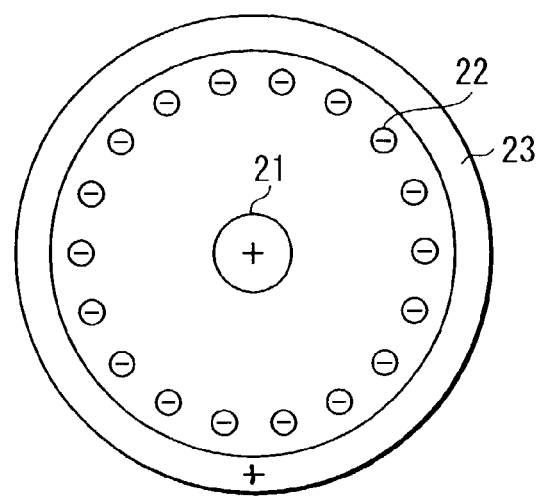

The polarities of the electrodes 21, 22, and 23 may change from the state shown in FIG. 5A to that of FIG. 5C, not to that of FIG. 5B. Specifically, as shown in FIG. 5C, the polarity of the voltage applied to the electrode 21 is inverted to positive, the polarity of the voltage applied to the electrode 22 is inverted to negative, and the polarity of the voltage applied to the electrode 23 is inverted to positive. Note that, in a modification of this embodiment, the polarity of the electrode 21 may be negative in FIG. 5C. Since the electrode 21 has positive polarity, there will result a more enhanced effect of separating the gene entangled on the electrode 22 from it. However, some unnecessary genes still remain in a central portion and it will be necessary to wash them off later in a separate step. If the electrode 21 has negative polarity, these unnecessary genes entangled on the electrode 22 are attracted towards the electrode 23 located on an outer side. Thus, the washing step that has to be carried out later is facilitated. It is preferable that the polarity of the electrode 21, whether it should be set to positive or negative, be determined in consideration of the design of the overall system including the washing step. In the case shown in FIG. 5C as well, it is possible to remove uncombined genes from the electrode 22 and thereby perform the hybridization with a high degree of efficiency.

According to the above description of the operation, as shown in FIGS. 5A and 5B, voltages whose polarity (negative polarity) is the same as the charge polarity of the detection target gene are applied to all the electrodes 22. Through the use of the arrangement in which the electrodes 22 are arrayed on the circumference, a gene in a sample liquid may be sequentially moved on the electrodes 22 in the array direction (circumferential direction) by dynamically switching the polarity of the voltage applied to the electrodes 22.

Figure 6A:
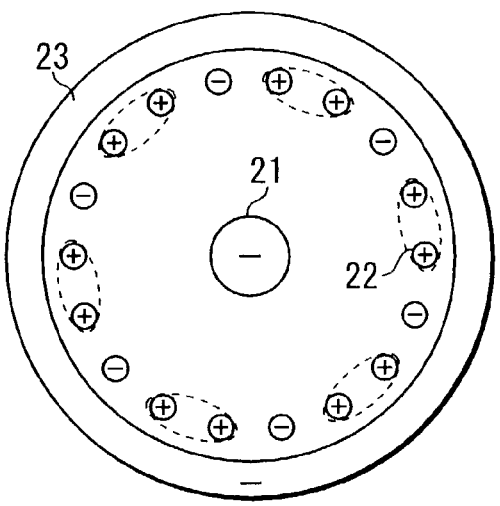
FIGS. 6A to 6C are views for explaining the movement of a detection target biological material on working electrodes in the biological material detection element according to the first embodiment.

This operation will be described below with reference to FIGS. 6A to 6C. As shown in FIG. 6A, positive voltages are applied to pairs of adjacent electrodes, of the electrodes 22, which are enclosed with the dotted lines, and negative voltages are applied to the electrodes adjacent to the pairs. The polarities of the voltages applied to the electrodes 22 are arranged like "positive—positive—negative—positive—positive—negative—positive—positive—negative—positive . . . "when viewed from the circumferential direction, i.e., the array direction of the electrodes 22.

Figure 6B:
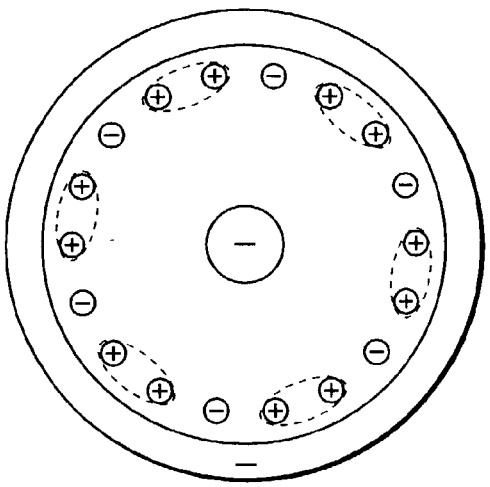

After an elapse of a predetermined unit time, as shown in FIG. 6B, the position of each pair of electrodes to which positive voltages are to be applied is shifted by one electrode, and the position of each electrode which is adjacent to each pair of electrodes and to which a negative voltage is to be applied is shifted by one electrode accordingly. When the predetermined unit time has further elapsed, the position of each pair of electrodes to which positive voltages are to be applied and the position of each electrode to which a negative voltage is to be applied are shifted by one electrode, as shown in FIG. 6C. In the case shown in FIGS. 6B and 6C, the position of each pair of electrodes to which positive voltages are to be applied and the position of each electrode to which a negative voltage is to be applied are shifted clockwise. Subsequently, such switching of the polarities of applied voltages will be done every unit time, i.e., in a predetermined cycle.

By applying voltages to the electrodes 22 while switching the polarities in this manner, a detection target biological material (e.g., a gene) in a sample liquid is moved on the array of the electrodes 22 in the circumferential direction. This allows the biological material uniformly and efficiently reacts to a ligand (e.g., a DNA probe) immobilized to each electrode 22. That is, in the process of moving on the array of the electrodes 22, the detection target biological material is located, without fail, on the electrode to which the ligand having a complementary relationship with the detection target biological material is immobilized, and can react with the ligand.

In this case, since materials nonspecifically binding with electrodes, of the electrodes 22, to which voltages having the same polarity as that charge polarity of the detection target biological material are applied are forcibly removed, the detection precision of the detection target biological material (a gene in this case) trapped on the electrode 22 as a ligand immobilizing portion can be greatly improved.

Figure 6C:
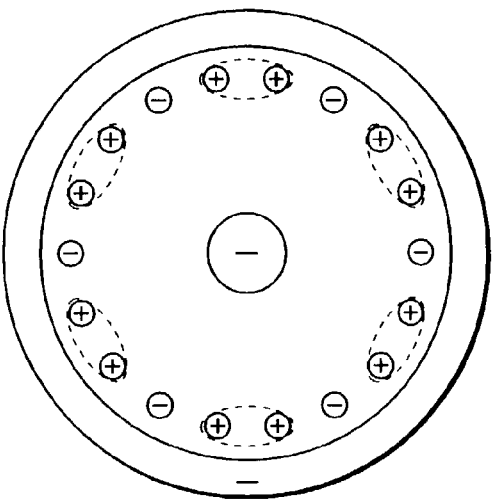

In the case shown in FIGS. 6A to 6C, voltages having the first polarity (negative polarity in the above case) are applied to each pair of adjacent electrodes of the electrodes 22, and a voltage having the second polarity (positive polarity in the above case) opposite to the first polarity is applied to each electrode adjacent to each pair of electrodes while the positions of electrodes to which such voltages are applied are shifted by one electrode at a time in the circumferential direction of the electrodes 22. However, the present invention is not limited to this. Letting n be the number of electrodes to which voltages having the first polarity are applied, m be the number of electrodes to which voltages having the second polarity are applied, and p be the number of electrodes by which the voltage application positions are shifted when the polarities of applied voltages are switched, n, m, and p can take arbitrary numbers equal to or larger than one. Most simply, it suffices if n=m=p=1. In this case, the polarity of an applied voltage is periodically and alternately switched between positive polarity and negative polarity from the viewpoint of one electrode 22.

The electrode arrangement of a biological material detection element according to a modification of the first embodiment will be described next with reference to FIGS. 7A to 7C.

In the biological material detection element shown in FIGS. 7A to 7C, a circular electrode 31 functioning as a counterelectrode is placed on the central portion, and an annular electrode 34A is placed on the outer circumferential side of the electrode 31 at a predetermined distance. Another annular electrode 34B is placed on a circumference located on the outer circumferential side of the electrode 34A at a predetermined distance. As in the above embodiment, a plurality of circular electrodes 32 are arrayed at a predetermined pitch. These electrodes 32 function as working electrodes. In addition, annular electrodes 33A and 33B are sequentially arranged on the outer circumferential side of the electrodes 32 at predetermined distances. These electrodes 33A and 33B function as reference electrodes.

In this embodiment, a detection target biological material in a sample liquid can be concentrated and moved on a peripheral portion by switching the polarities of voltages applied to the electrodes 31, 34A, 34B, 32, 33A, and 33B using a driving circuit (not shown), as shown in FIGS. 7A to 7C.

First of all, as shown in FIG. 7A, a negative voltage, positive voltage, and negative voltage are respectively applied to the electrode 31, electrode 34A, and electrode 34B. In addition, positive voltages are applied to the electrodes 32, and negative voltages are applied to the electrodes 33A and 33B. In this case, as in the above embodiment, a detection target biological material (e.g., a gene) with negative charge polarity in a sample liquid introduced onto the central portion of the biological material detection element moves to the peripheral portion due to the electrostatic repulsive force originating from the central electrode 31 to which a voltage having the same polarity as the charge polarity is applied.

In this case, a voltage having an opposite polarity to the charge polarity of the detection target biological material is applied to the electrode 34A located closer to the outer circumferential side than the electrode 31, and a voltage having the same polarity as the charge polarity is applied to the electrode 34B located closer to the outer circumferential side than the electrode 34A. With this operation, the detection target biological material that have moved from the electrode 31 onto the electrode 34A is trapped and concentrated on the electrode 34A due to the electrostatic attracting force produced by the electrode 34A and the electrostatic repulsive force produced by the electrode 31 and electrode 34B located on the two sides of the electrode 34A.

The polarity of the voltage applied to the electrode 34A and the polarity of the voltage applied to the electrode 34B are then inverted to negative polarity and positive polarity, respectively, by the driving circuit, as shown in FIG. 7B. The polarities of the voltages applied to the remaining electrodes 31, 32, 33A, and 33B are kept the same as those shown in FIG. 7A. The detection target biological material trapped on the electrode 34A in the state shown in FIG. 7A moves onto the electrode 34B due to the electrostatic repulsive force produced by the electrode 34A and the electrostatic attracting force produced by the electrode 34B in the state shown in FIG. 7B.

When the polarity of only the voltage applied to the electrode 34B in the state shown in FIG. 7B is inverted to negative polarity by the driving circuit as shown in FIG. 7C, the detection target biological material that has moved onto the electrode 34B moves onto the electrode 32 due to the electrostatic repulsive force produced by the electrodes 34A and 34B and the electrostatic attracting force produced by the electrode 32. In this state, the detection target biological material on the electrode 32 is trapped and concentrated on the electrode 32 due to the electrostatic attracting force produced by the electrode 32 and the electrostatic repulsive force produced by the electrodes 34A and 33A.

In this manner, the detection target biological material in the sample liquid introduced onto the central portion of the biological material detection element is sequentially concentrated and moved to the peripheral portion. Finally, the detection target biological material can be supplied in a concentrated state onto the electrode 32 on which the ligand is immobilized. According to this embodiment, since the detection target biological material is concentrated on the electrode 32 to which the ligand is immobilized, the detection target biological material and the ligand can be made to react with each other efficiently without amplifying the detection target biological material in advance by a gene amplification method such as the PCR method. This improves the detection efficiency.

In the biological material detection element according to another modification of the first embodiment, as in the above embodiment, a gene in a sample liquid may be sequentially moved on the electrodes 32 in the array direction (circumferential direction) by dynamically switching the polarity of a voltage applied to each electrode 32 serving as a working electrode, as shown in FIGS. 8A to 8C.

First of all, as shown in FIG. 8A, positive voltages are applied to each pair of adjacent electrodes, of the electrodes 32, which are enclosed with the dotted line, and a negative voltage is applied to each electrode adjacent to each pair of adjacent electrodes. After an elapse of a predetermined unit time, as shown in FIG. 8B, the position of each pair of adjacent electrodes to which positive voltages are to be applied is shifted by one electrode, and the position of each electrode adjacent to each pair of adjacent electrodes by one electrode accordingly. When the predetermined unit time has further elapsed, the position of each pair of adjacent electrodes to which positive voltages are to be applied and the position of each electrode to which a negative voltage is to be applied are shifted by one electrode, as shown in FIG. 8C. Subsequently, the polarities of applied voltages are switched every unit time, i.e., in a predetermined cycle, to allow the detection target biological material in the sample liquid to move on the array of electrodes 32 in the circumferential direction and efficiently react with the ligand immobilized to each electrode 32.

Figure 9:
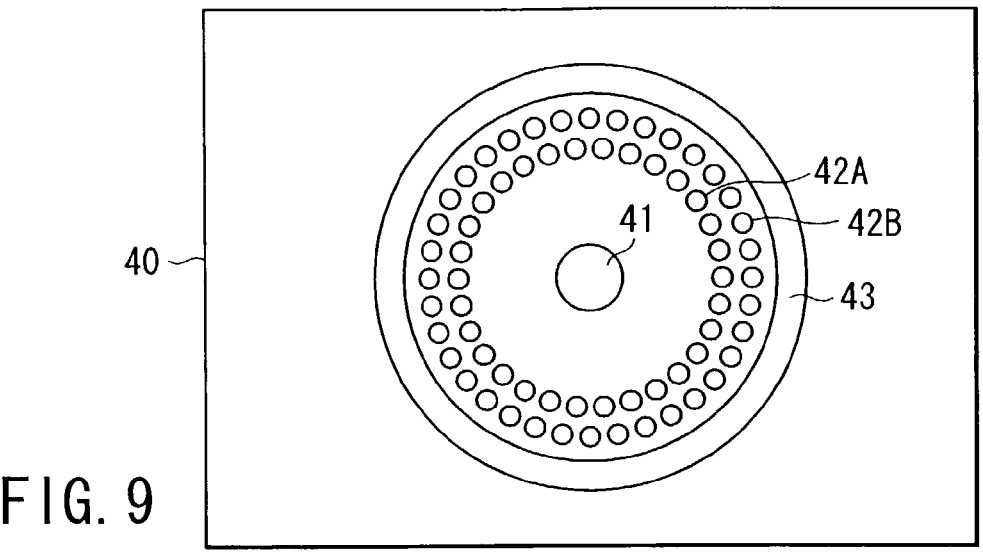
FIG. 9 is a plan view showing the arrangement of a biological material detection element according to still another modification of the first embodiment.

FIG. 9 shows the arrangement of a biological material detection element according to still another embodiment of the present invention.

In the biological material detection element according to this embodiment, a first electrode 41 having a circular shape and functioning as a counterelectrode is placed on a central portion on an element substrate 40, and a third electrode 43 having an annular shape and functioning as a reference electrode is placed on a peripheral portion as in the above two embodiments. This embodiment differs from the above embodiments in that second electrodes 42A and 42B functioning as working electrodes are arrayed on two concentric circumferences. In this case, electrodes serving as working electrodes are formed in two arrays. However, three or more arrays of electrodes may be formed.

By forming a plurality of arrays of electrodes serving as working electrodes in this manner, the ligand immobilized to each electrode and a detection target biological material can be made to reach with each other more reliably, thus further improving the detection efficiency.

Figure 10:
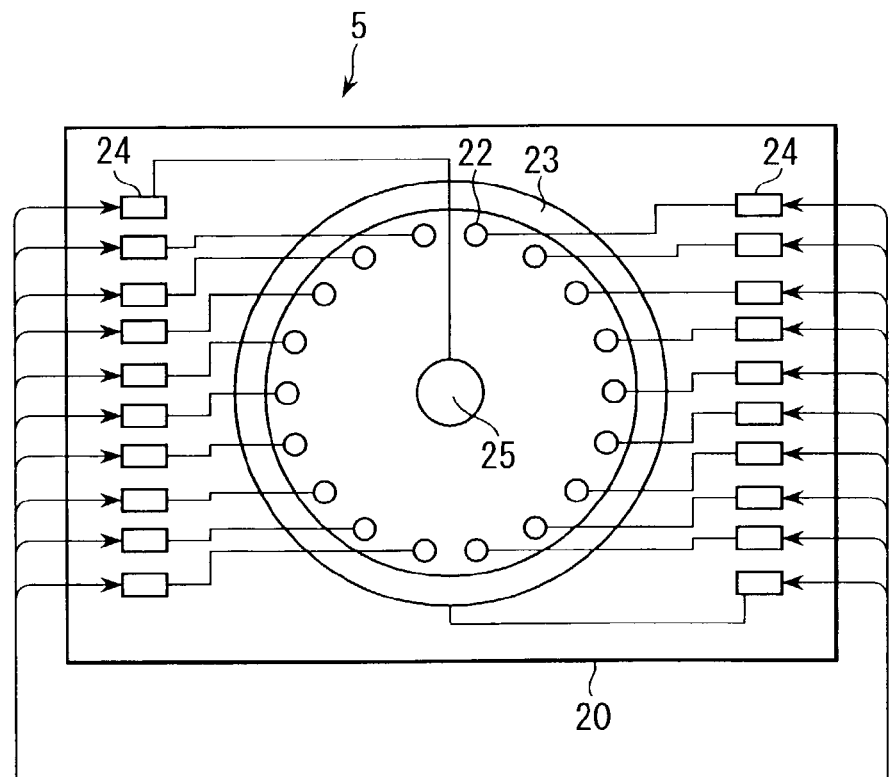
FIG. 10 is a plan view of a biological material detection element according to still another modification of the first embodiment, showing how a driving circuit is connected to the biological material detection element.

FIG. 10 is a plan view of a biological material detection element according to still another modification of the first embodiment showing how a driving circuit is connected to the biological material detection element. A biological material detection element 5 according to this embodiment, the first electrode 21 described in the above embodiment is omitted, and a position where the electrode 21 is removed, i.e., the central portion of the array of second electrodes 22, serves as a sample liquid receiving portion 25. In addition, as the electrode 21 is removed, the interconnections between the electrode 21 and a driving circuit 5 are removed.

In the above embodiment, as described with reference to, for example, FIG. 5A, when a negative voltage whose polarity is the same as the charge polarity of a gene is applied to the first electrode 21, and a positive voltage whose polarity is opposite to the charge polarity of the gene is applied to each second electrode 22, the sample liquid supplied onto the electrode 21 receives the electrostatic repulsive force produced by the charge polarity of the gene and the electrode 21. This makes it easy to move the sample liquid radially toward the electrodes 22 on the peripheral portion.

If a negative pressure applied to the sample liquid is increased to a certain degree when the sample liquid is to be discharged outside from the sample liquid outlet 4 described above, the sample liquid supplied to the sample liquid receiving portion 25 can be moved toward the electrode 22 side by only the electrostatic attracting force produced by the second electrodes 22 without using the electrostatic repulsive force produced by the first electrode 21 as in the above embodiment.

In addition, a similar modification can also be applied to the arrangements shown in FIGS. 7A to 9. For example, the first electrode 31 in FIGS. 7A to 8C or the first electrode 41 in FIG. 9 may be removed, and a sample liquid receiving portion can be formed at the position where the electrode 31 or 41 is removed.

A sample to be processed by the biological material detection element or biological material detection apparatus according to the embodiment may be, but is not limited to, for example, blood, blood serum, leukocyte, urine, stool, sperm, saliva, tissue, cultured cell, expectoration, and the like. If a detection target biological material is a gene, the gene is extracted from these samples. The extraction method may be, but is not limited to a liquid-liquid extraction method such as a phenol-chloroform method or a solid liquid extraction method using a carrier. Alternatively, a commercially available nucleic acid extraction method such as QIAamp (available from QIAGEN), SUMAI test (available from Sumitomo Metal Industries, Ltd.) can be used.

The gene sample solution extracted in this manner is then introduced onto the biological material detection element (DNA chip) described in the above embodiment, and a hybridization reaction is caused on an electrode to which a DNA probe as a ligand is immobilized. A buffering solution that falls within the range of ion intensities of 0.01 to 5 and the range of pH5 to pH10 is used as a reaction solution. A hybridization accelerating agent such as dextran sulfate, salmon sperm DNA, bovine thymus DNA, EDTA, or surfactant can be added to this solution, as needed. The extracted sample gene is added to this solution. The solution must be heat-denatured at 90° C. or more before introduction into the biological material detection element. An unreacted sample gene can be recovered from the sample liquid outlet 4 to be introduced into the biological material detection element again, as needed.

The extracted gene can be detected by marking in advance it with a fluorescent dye such as FITC, Cy3, Cy5, or rhodamine, an enzyme such as biotin, hapten, oxidase, or phosphatase, or an electrochemically active material such as ferrocene or quinones, or by using a second probe marked with such a material. If the gene is marked with a fluorescent dye, it can be optically detected.

When the gene is to be detected by using an electrochemically active DNA binder, detection is done by the following procedure.

A DNA binder which selectively combines with a double stranded DNA portion is made to react with the double stranded DNA portion formed on the surface of an electrode (working electrode) to which a DNA probe is immobilized, thereby performing electrochemical measurement. The DNA binder to be used in this case is, but is not limited to, for example, Hoechst 33258, acridine orange, quinacrine, downomycin, metallointercalator, bis-intercalator such as bis-acridine, tris-intercalator, or polyintercalator. In addition, such an intercalator can be modified in advance by an electrochemically active metal complex such as ferrocene or viologen.

Although the concentration of a DNA binder varies depending on the type of material, the material is generally used within the range of 1 ng/mL to 1 mg/mL. In this case, a buffering agent within the range of ion intensities of 0.001 to 5 and the range of pH5 to pH10 is used.

After an electrode serving as a working electrode and a DNA binder are made to react with each other, cleaning is performed, and electrochemical measurement is performed. Electrochemical measurement is performed by a triple electrode type including a reference electrode, counterelectrode, and working electrode or a double electrode type including a counterelectrode and working electrode. In measurement, a potential equal to or higher than a potential at which the DNA binder reacts is applied, and a reaction current value originating from the DNA binder is measured. In this case, the potential is swept at a constant velocity or pulses or a constant potential can be applied. In measurement, currents and voltages are controlled by using a potentiostat, digital multimeter, function generator, and the like.

EXAMPLE 1

The biological material detection element described with reference to FIGS. 1 to 3C and 7A to 8C was formed into an electrode-integrated interferon curative effect predicting DNA chip and the following experiment was conducted.

First of all, a chromosome DNA was extracted from human leukocyte, a MxA gene fragment of about 100 bp was PCR-amplified by using a proper primer. The amplified fragment was heat-denatured. The resultant fragment was then introduced into the DNA chip. Note that a DNA probe associated with SNP (single nucleotide polymorphism) existing in the MxA gene was immobilized in advance on an electrode 32 of the DNA chip. After the sample was introduced, it was left standing for two hr, and cleaning was done with a buffering agent. When a DNA binder (Hoechst 33258) was made to act, it was found that an interferon curative effect could be predicted even if the charge was not electrically controlled. However, it became clear that the results vary depending on the manner in which the liquid flowed.

In contrast to this, it was found that when the introduced gene was moved to the peripheral portion while being concentrated by switching the polarities of voltages applied to the respective electrodes, as shown in FIGS. 8A to 8C, and the gene was moved on the array of electrodes 32 by switching the polarities of voltages applied to the respective electrodes 32 while the gene was trapped on the electrode 32, as shown in FIGS. 7A to 7C, a curative effect could be accurately predicted without performing PCR amplification.

EXAMPLE 2

A biological material detection element similar to that described in the embodiments was formed into an electrode separate type biological material detection chip, and the following experiment was conducted.

Antibodies for various human tumor markers were immobilized to a nylon film in advance. Electrodes were then arranged under the film so as to be in contact therewith. When a tumor marker was detected by using human serum as a sample, it was found that the marker could be detected with high reproducibility and high sensitivity on the order of 0.1 ng/mL. In this case, an antibody marked with horseradish peroxidase was used as the second antibody, and a framework for luminescence detection was used.

SECOND EMBODIMENT

Figure 11:
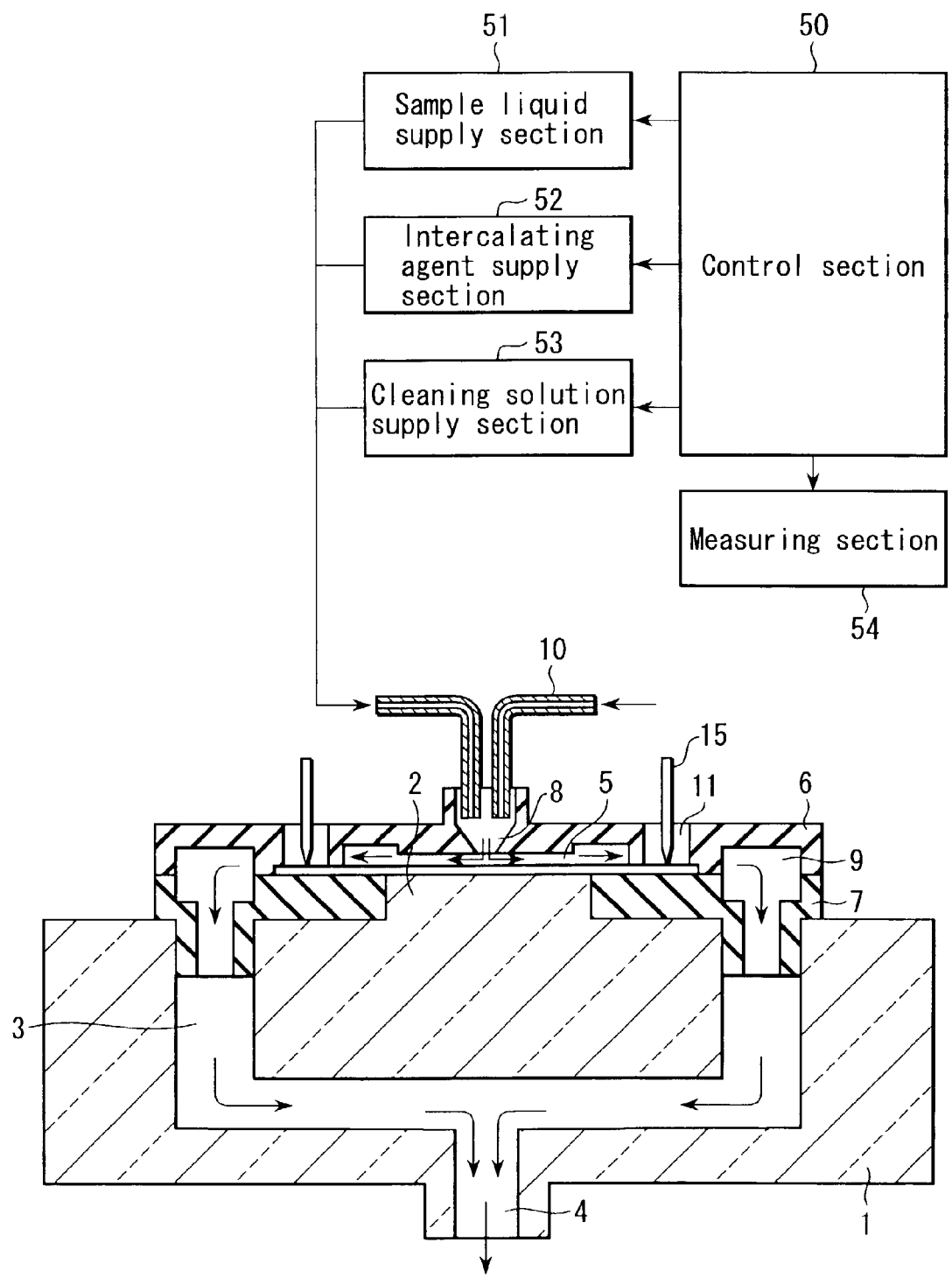
FIG. 11 is a sectional view showing the arrangement of a biological material detection apparatus including a biological material detection element according to a second embodiment of the present invention.

FIG. 11 is a sectional view showing the arrangement of a biological material detection apparatus including a biological material detection element according to a second embodiment of the present invention. A base 1 has a protruding element mount portion 2 on its central upper portion on which a biological material detection element 5 is mounted. The base 1 also has a liquid passage hole 3 in the two sides in FIG. 1 which allows a sample liquid, intercalating agent, cleaning solution, or the like to pass through and a liquid outlet 4 in a central lower portion which communicates with the liquid passage hole 3. An upper holder 6 and lower holder 7 are mounted on the base 1. The upper and lower holders hold the biological material detection element 5 mounted on the element mount portion 2 from both upper and lower sides, and mainly guide a liquid into the element 5 and the liquid passing through the element 5 into the liquid passage hole 3. A liquid introduction portion 8 is formed in the central portion of the upper holder 6. The distal end of a liquid supply pipe 10 is connected to this liquid introduction portion 8. One of a sample liquid supply section 51, intercalating agent supply section 52, and cleaning solution supply section 53 which are controlled by a control section 50 is selectively connected to the liquid supply pipe 10. A measuring section 54 controlled by the control section 50 measures an electrochemical signal by using an intercalating agent and outputs the detection result on a biological material, as will be described later. The liquid introduced from the liquid supply pipe 10 into the liquid introduction portion 8 is guided onto the biological material detection element 5 and used for the detection of a biological material. Thereafter, the liquid is discharged outside from a liquid outlet 4 through a liquid guide duct 9 formed by the lower and upper holders 6 and 7 and the liquid passage hole 3 formed in the base 1. A rectangular through hole 11 is formed in the upper holder 6. The distal end of a contact electrode 15 can be brought into contact with an electrode serving as a working electrode on the biological material detection element 5 by inserting the contact electrode 15 via the through hole 11. By using this contact electrode 15, a biological material detection signal can be extracted as an electrical signal such as a current or potential signal.

In the biological material detection apparatus shown in FIG. 11, the detailed arrangements of the upper and lower holders 6 and 7 are the same as those shown in FIGS. 2A to 3C. The detailed arrangement of the biological material detection element 5 is also the same as that shown in FIG. 4. As described above, when a detection target biological material is a gene, a DNA probe is immobilized as a ligand to an electrode 22. The genes in the sample liquid are converted into a single stranded gene in advance. Only a gene having a specific sequence is trapped on the electrode 22 in correspondence with the DNA probe immobilized to the electrode 22. Subsequently, the DNA probe and gene complementarily combine with each other (hybridization). Furthermore, the same materials and methods as those described above with reference to FIG. 4 are used as a substrate material used for an element substrate 20, electrode materials used for an electrode 21, the electrodes 22, and an electrode 23, methods of forming the electrodes 21, 22, and 23, an insulating material used for a thin insulating film that covers the surfaces of the electrodes 21, 22, and 23, and the like.

A procedure for detecting a biological material in this embodiment will be described below with reference to the flow chart of FIG. 12.

First of all, the sample liquid supply section 51 supplies a sample liquid containing a detection target biological material to the liquid supply pipe 10 under the control of the control section 50 (step S1). The sample liquid supplied to the liquid supply pipe 10 is introduced onto the biological material detection element 5 via the liquid introduction portion 8 and moved from the electrode 21 to the electrodes 22 and electrode 23 (see FIG. 4) by the electrostatic force produced by the electrodes 21 to 23 to which predetermined voltages are applied from a driving circuit 25. Finally, the sample liquid is separated from the biological material detection element 5 and discharged from the liquid outlet 4 via the liquid guide duct 9 and liquid passage hole 3.

In this process, the sample liquid adheres to the ligand immobilized to the electrode 22, and hybridization is performed. More specifically, when, for example, a detection target biological material is a gene, and a ligand is a DNA probe, i.e., a single stranded DNA that reacts with a specific gene, the DNA in the sample liquid is converted into single stranded DNA when the sample liquid adheres to the DNA probe.

The first cleaning is then performed (step S2). In this first cleaning step, the cleaning solution supply section 53 supplies a cleaning solution to the liquid supply pipe 10 under the control of the control section 50. With this operation, an unnecessary sample liquid in the biological material detection apparatus, and more specifically, a sample liquid other than the sample liquid (biological material) adhering to the electrode 22 is cleaned and removed. The removed unnecessary sample liquid is discharged, together with the cleaning solution.

Subsequently, the intercalating agent supply section 52 supplies an intercalating agent for improving the detection sensitivity of a biological material, e.g., a nucleic acid intercalating agent that specifically reacts to double stranded DNA, to the liquid supply pipe 10 under the control of the control section 50 (step S3). The second cleaning is then performed (step S4).

In the second cleaning step, the cleaning solution supply section 53 supplies a cleaning solution to the liquid supply pipe 10 under the control of the control section 50. With this operation, an unnecessary sample liquid, and more specifically, a sample liquid other than the sample liquid adhering to the electrode 22 is cleaned and removed. The removed unnecessary sample liquid is discharged, together with the cleaning solution, via the cleaning solution discharge route in the sample liquid supply processing in step S1.

The measuring section 54 applies a voltage between the electrode 21 as a counterelectrode and the electrode 22 as a working electrode under the control of the control section 50. The measuring section 54 measures a current flowing via the two electrodes 21 and 22, i.e., an oxidation current that enters the bond portion between the ligand immobilized to the electrode 22 and the specific biological material and is obtained from an intercalating agent adhering to the bond portion, thereby measuring an electrochemical signal by using the intercalating agent (step S5).

The third cleaning step is performed (step S6). In the third cleaning step, the cleaning solution supply section 53 supplies a cleaning solution to the liquid supply pipe 10 under the control of the control section 50. In this case, all the intercalating agent including the intercalating agent that adheres to the ligand immobilized to the electrode 22 and has contributed to the measurement of the electrochemical signal is cleaned and removed.

Of steps S1 to S6, steps S3 to S6 are repeatedly executed until it is determined in step S7 that the number of times of execution reaches a predetermined number of times. That is, a series of steps, i.e., (a) supply of an intercalating agent, (b) current measurement (measurement of electrochemical signal by the intercalating agent), and (c) removal of the intercalating agent adhering to the ligand, is repeated.

The set traffic capacity 34 integrates a plurality of measurement results obtained in this series of steps, i.e., current (oxidation current) values dependent on a detection target biological material. With this operation, only electrochemical signals originating from the intercalating agent dependent on the detection target biological material are integrated, and random noise components such as background currents are canceled in the process of integration. This makes it possible to detect a specific biological material with high sensitivity.

Figure 13:
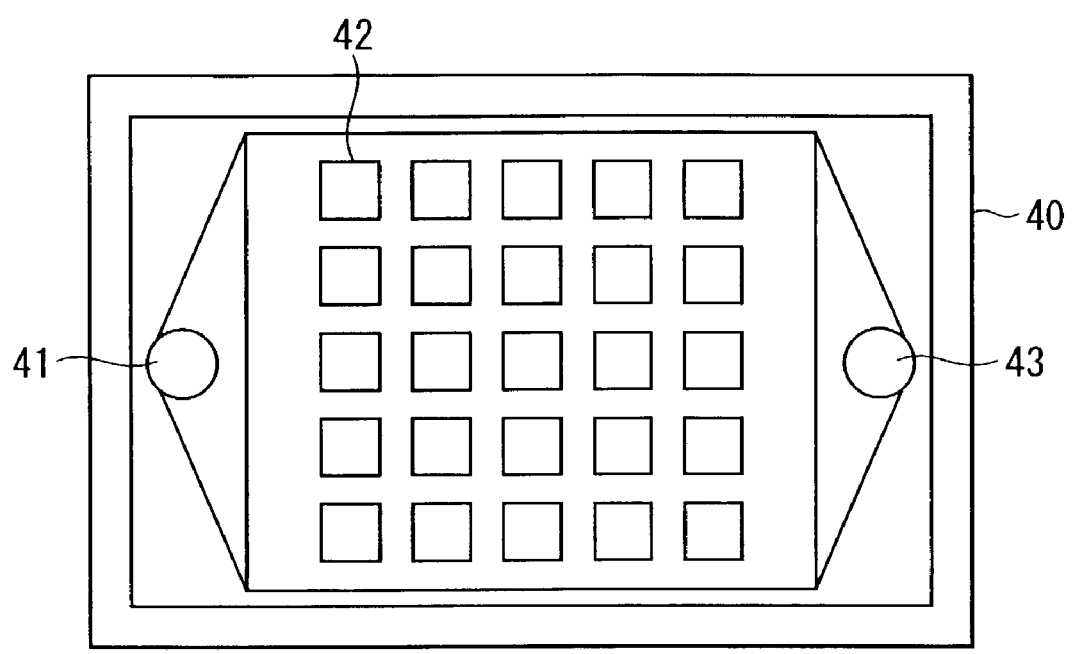
FIG. 13 is a plan view showing the arrangement of a biological material detection element according to a modification of the second embodiment.

FIG. 13 is a plan view showing the arrangement of a biological material detection element according to a modification of the second embodiment.

In the biological material detection element according to this embodiment, a liquid introduction portion 41 is formed at one end portion (the left end in FIG. 13) on an element substrate 40, and a liquid discharge portion 43 is formed at the other end (the right end in FIG. 13), and electrodes 42 serving as working electrodes are arrayed in the central portion in the form of a matrix. A sample liquid, intercalating agent, or cleaning solution is introduced from the liquid introduction portion 41. This liquid is discharged from the liquid discharge portion 43 after moving on the electrodes 42.

Figure 12:
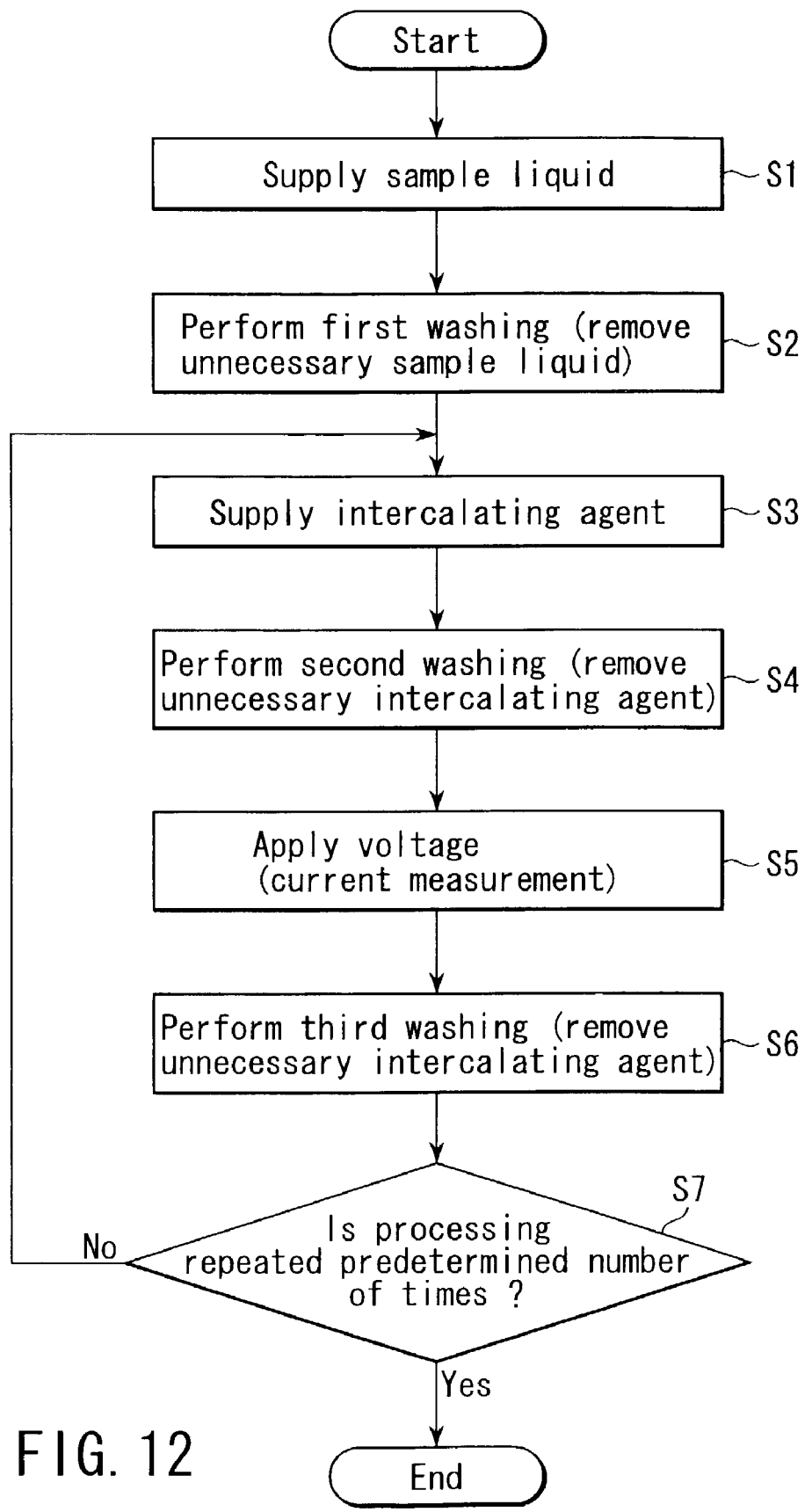
FIG. 12 is a flow chart for explaining a biological material detection procedure in the second embodiment.

Even with the use of a biological material detection element having such an arrangement, the same effects as those of the above embodiment can be obtained by performing the steps in the procedure shown in FIG. 12.

A sample to be processed by the biological material detection element or biological material detection apparatus according to the embodiment is, but is not limited to, for example, blood, blood serum, leukocyte, urine, stool, sperm, saliva, tissue, cultured cell, expectoration, and the like. If, for example, a detection target biological material is a gene, the gene is extracted from these samples. An extraction method is not specifically limited. A liquid-liquid extraction method such as a phenol-chloroform method or a solid liquid extraction method using a carrier can be used. Alternatively, a commercially available nucleic acid extraction method such as QIAamp (available from QIAGEN), SUMAI test (available from Sumitomo Metal Industries, Ltd.) can be used.

The gene sample solution extracted in this manner is then introduced onto the biological material detection element (DNA chip) described in the above embodiment, and a hybridization reaction is caused on an electrode to which a DNA probe as a ligand is immobilized. A buffering solution that falls within the range of ion intensities of 0.01 to 5 and the range of pH5 to pH10 is used as a reaction solution. A hybridization accelerating agent such as dextran sulfate, salmon sperm DNA, bovine thymus DNA, EDTA, or surfactant can be added to this solution, as needed. The extracted sample gene is added to this solution. The solution must be heat-denatured at 90° C. or more before introduction into the biological material detection element. An unreacted sample gene can be recovered from the sample liquid outlet 4 to be introduced into the biological material detection element again, as needed.

The extracted gene can be detected by marking in advance it with a fluorescent dye such as FITC, Cy3, Cy5, or rhodamine, an enzyme such as biotin, hapten, oxidase, or phosphatase, or an electrochemically active material such as ferrocene or quinones, or by using a second probe marked with such a material. If the gene is marked with a fluorescent dye, it can be optically detected.

When the gene is to be detected by using an electrochemically active DNA binder, detection is done by the following procedure.

A DNA binder which selectively combines with a double stranded DNA portion is made to react with the double stranded DNA portion formed on the surface of an electrode (working electrode) to which a DNA probe is immobilized, thereby performing electrochemical measurement. The DNA binder to be used in this case is, but is not limited to, for example, Hoechst 33258, acridine orange, quinacrine, downomycin, metallointercalator, bis-intercalator such as bis-acridine, tris-intercalator, or polyintercalator. In addition, such an intercalator can be modified in advance by an electrochemically active metal complex such as ferrocene or viologen.

Although the concentration of a DNA binder varies depending on the type of material, the material is generally used within the range of 1 ng/mL to 1 mg/mL. In this case, a buffering agent within the range of ion intensities of 0.001 to 5 and the range of pH5 to pH10 is used.

After an electrode serving as a working electrode and a DNA binder are made to react with each other, cleaning is performed, and electrochemical measurement is performed. Electrochemical measurement is performed by a triple electrode type including a reference electrode, counterelectrode, and working electrode or a double electrode type including a counterelectrode and working electrode. In measurement, a potential equal to or higher than a potential at which the DNA binder reacts is applied, and a reaction current value originating from the DNA binder is measured. In this case, the potential is swept at a constant velocity or pulses or a constant potential can be applied. In measurement, currents and voltages are controlled by using a potentiostat, digital multimeter, function generator, and the like.

EXAMPLE 3

The biological material detection element 5 shown in FIG. 11 was formed into a current detection type interferon curative effect predicting DNA chip, and the following experiment was conducted.

First of all, a chromosome DNA was extracted from human leukocyte, a MxA gene fragment of about 100 bp was PCR-amplified by using a proper primer. The amplified fragment was heat-denatured. The resultant fragment was then introduced into the DNA chip. Note that a DNA probe associated with SNP (single nucleotide polymorphism) existing in the MxA gene was immobilized in advance on an electrode 32 of the DNA chip. After the sample was introduced, it was left standing for two hr, and cleaning was done with a buffering agent. When a DNA binder (Hoechst 33258) was made to act, it was found that an interferon curative effect could be predicted even if the charge was not electrically controlled. However, it became clear that the results vary depending on the manner in which the liquid flowed.

In contrast to this, it was found that a curative effect could be predicted with high sensitivity and high accuracy without performing PCR amplification by the following operation. The introduced gene was moved to the peripheral portion while being concentrated by switching the polarities of voltages applied to the respective electrodes, as shown in FIGS. 8A to 8C, and the gene was moved on the array of electrodes 32 by switching the polarities of voltages applied to the respective electrodes 32 while the gene was trapped on the electrode 32, as shown in FIGS. 7A to 7C. In addition, as described with reference to FIG. 12, the series of steps S3 to S6 is repeated a plural times.

THIRD EMBODIMENT

This embodiment relates to a charged material moving apparatus for moving a charged material such as a biological material, e.g., a gene or protein and, more particularly, to a charged material moving apparatus suitable for a biological material detection apparatus. This embodiment provides a charged material moving apparatus which can move a charged material such as a biological material to make the material efficiently react with each ligand on a charged material detection element. In addition, there is provided a charged material moving apparatus which can concentrate a detection target charged material in a sample and attain an improvement in detection sensitivity when used for a biological material detection apparatus.

Figure 14:
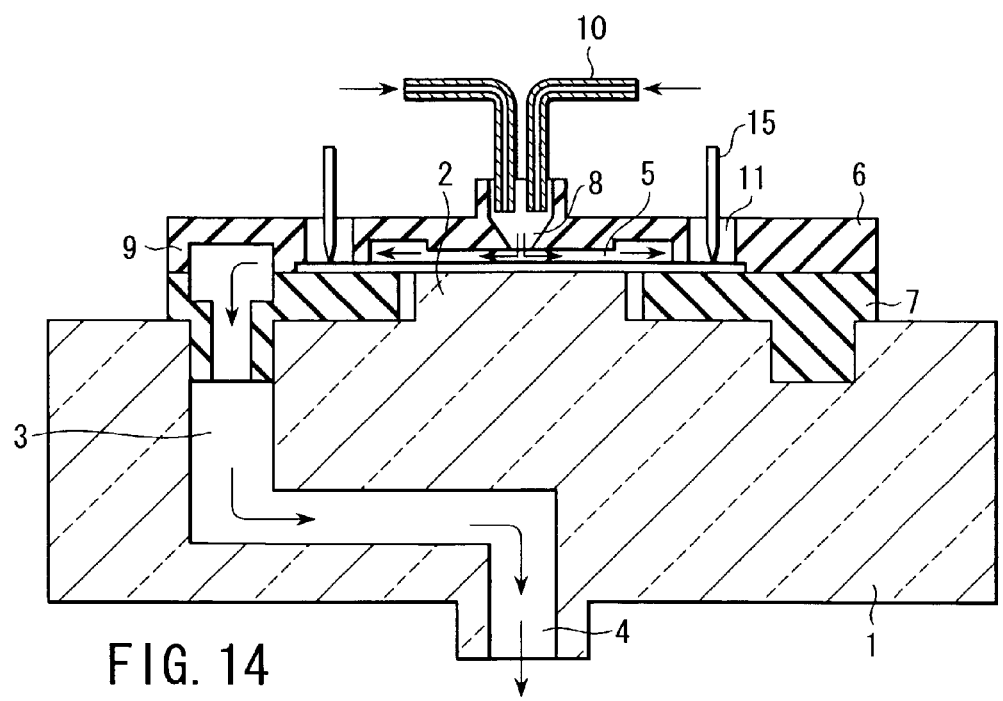
FIG. 14 is a sectional view showing the arrangement of a biological material detection apparatus, to which a charged material moving apparatus is applied, according to a third embodiment of the present invention.

FIG. 14 is a sectional view showing the arrangement of a biological material detection apparatus, to which a charged material moving apparatus is applied, according to a third embodiment of the present invention. A base 1 has a protruding element mount portion 2 on its central upper portion on which a biological material detection element 5 (to be described in detail later) is mounted. The base 1 also has a sample liquid passage hole 3 in the two sides in FIG. 14 and a sample liquid outlet 4 in a central lower portion which communicates with the sample liquid passage hole 3.

An upper holder 6 and lower holder 7 are mounted on the base 1. The upper and lower holders hold the biological material detection element 5 mounted on the element mount portion 2 from both upper and lower sides, and mainly guide a sample liquid into the element 5 and the sample liquid passing through the element 5 into the sample liquid passage hole 3. The structures of the upper and lower holders 6 and 7 will be described in detail later.

A sample liquid introduction portion 8 is formed in the central portion of the upper holder 6. A sample liquid supply pipe 10 is connected to this sample liquid introduction portion 8. The sample liquid introduced from the sample liquid supply pipe 10 into the sample liquid introduction portion 8 is guided onto the biological material detection element 5 and used for the detection of a biological material. Thereafter, the sample liquid is discharged outside from a sample liquid outlet 4 through a sample liquid guide duct 9 formed by the lower and upper holders 6 and 7 and the sample liquid passage hole 3 formed in the base 1.

A rectangular through hole 11 is formed in the upper holder 6. The distal end of a contact electrode 15 can be brought into contact with an electrode serving as a working electrode on the biological material detection element 5 by inserting the contact electrode 15 via the through hole 11. By using this contact electrode 15, a biological material detection signal can be extracted as an electrical signal such as a current or potential signal.

Figure 15:
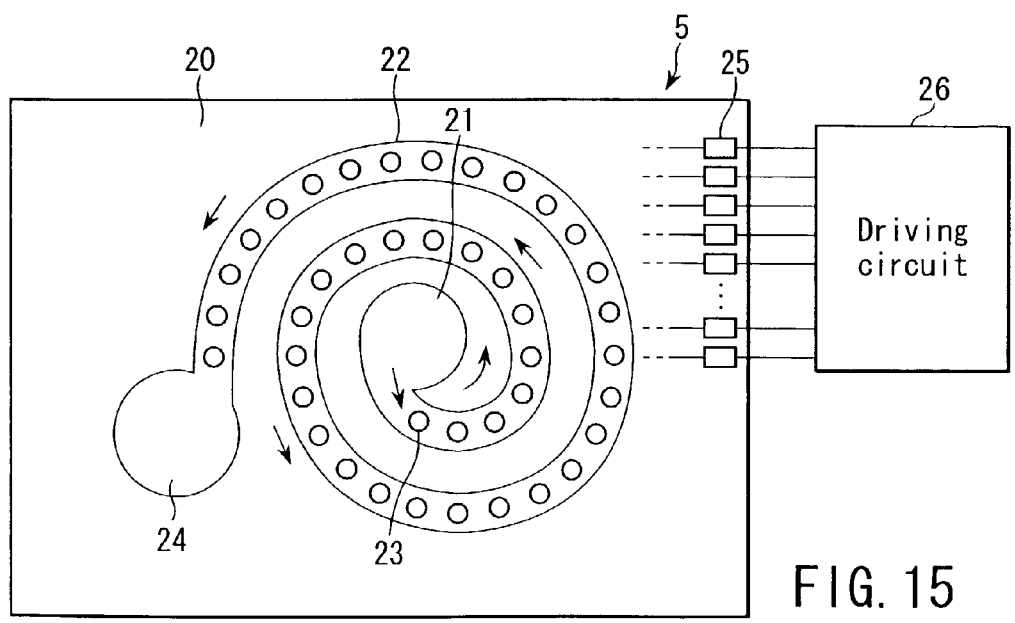
FIG. 15 is a plan view showing the schematic arrangement of a biological material detection element according to the third embodiment.

FIG. 15 is a plan view showing the arrangement of the biological material detection element 5. A sample liquid receiving portion 21 formed from a recess portion is formed immediately under the sample liquid introduction portion 8 on an element substrate 20 shown in FIG. 14. A spiral sample liquid guide groove 22 having one end communicating with the sample liquid receiving portion 21 is formed on the element substrate 20. A plurality of circular electrodes 23 functioning as working electrodes are arrayed on the bottom portion of the guide groove 22 along the spiral. A sample liquid discharge portion 24 is formed at the other end of the guide groove 22 of the element substrate 20. This sample liquid discharge portion 24 communicates with a sample liquid guide duct 9 shown in FIG. 14.

At least one type of specific detection ligand is immobilized to each electrode 23. That is, each electrode 23 also serves as a ligand immobilizing portion. The ligand immobilized to each electrode 23 is selected from one of a gene, gene probe, protein, protein fragment, coenzyme, receptor, and sugar chain in accordance with the biological material to be detected.

If different ligands are immobilized to the respective electrodes 23, a plurality of biological materials can be detected at once. In addition, if identical ligands are immobilized to the respective electrodes 23, many biological materials can be detected at once. If many electrodes 23 (ligand immobilizing portions) are patterned on the element substrate 20 in advance by photolithography, the productivity of biological material detection elements 5 improves.

The electrodes 23 are connected to electrode pads 25 via a multilayer interconnection formed on the element substrate 20. A driving circuit 26 for driving the electrodes 23 by applying predetermined voltages thereto is connected to the electrode pads 25. The operation of this driving circuit 26 will be described in detail later.

The sample liquid supplied from the sample liquid supply pipe 10 in this manner is guided by the upper holder 6 and lower holder 7 and introduced from the central portion into the biological material detection element 5. After the sample liquid is uniformly supplied to the ligand immobilizing portions formed on the peripheral portion of the element 5, the liquid is discharged from below. Detection of a biological material in the sample liquid can therefore be done under a uniform condition.

If a biological material to be detected is a gene, a DNA probe is immobilized as a ligand to the electrode 23. As is known, a DNA probe is a single stranded gene that reacts with a specific gene. If genes in a sample liquid are converted into a single stranded gene in advance, only a gene having a specific sequence in correspondence with the DNA probe immobilized to the electrode 23 is trapped by the electrode 23. Subsequently, the DNA probe and the gene are complementarily bound to each other (hybridization).

The above arrangement will be described in further detail. First of all, a substrate material used for the element substrate 20 is, but is not limited to, for example, an inorganic insulating material such as glass, silica glass, alumina, sapphire, forsterite, silicon carbide, silicon oxide, or silicon nitride. Alternatively, one of the following organic materials can be used as a substrate material: polyethylene, ethylene, polypropylene, polyisobutylene, polymethylmethacrylate, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, a styrene-acrylonitrile copolymer, an acrylonitrile-butadiene-styrene copolymer, silicone resin, polyphenylene oxide, polysulfone, and the like. In addition, if biological material detection is to be performed by the optical method to be described later, a thin fiber film such as nylon or cellulose can be used.

The electrode material to be used for the electrodes 23 is not specifically limited. As a material for an electrode including ligand immobilizing spot, when biological material detection is to be performed electrochemically, for example, one of the following materials can be used: a single metal such as gold, gold alloy, silver, platinum, mercury, nickel, palladium, silicon, germanium, gallium, or tungsten, alloys each containing at least two of these metals, carbon such as graphite or glassy carbon, oxides thereof, compounds thereof, semiconductor compounds such as silicon oxide, and various kinds of semiconductor devices such as a CCD, FET, and CMOS.

As a method of forming the electrodes 23, plating, printing, sputtering, vapor deposition, or the like can be used. As a vapor deposition method, one of a resistance-heating method, RF heating method, and electron beam heating method can be used. As a sputtering method, one of DC bipolar sputtering, bias sputtering, asymmetrical AC sputtering, getter sputtering, and RF sputtering can be used. For an electrode, an electrolytic polymer film or conductive high polymer such as polypyrrole or polyaniline can be used.

An insulating material used for a thin insulating film that covers the surfaces of the electrodes 23 is, but is not limited to, for example, photopolymer or photoresist material. As a photoresist material, an exposure photoresist, far ultraviolet photoresist, X-ray photoresist, or electron beam photoresist may be used. A main material for an exposure photoresist includes cyclized rubber, polycinnamic acid, and novolac resin. As a far ultraviolet photoresist, cyclized rubber, phenol resin, polymethylisopropenylketone (PMIPK), polymethylmethacrylate (PMMA), or the like may be used. As an X-ray photoresist, a material written in "Thin Film Handbook" (Ohmsha, Ltd.) as well as a COP and metal acrylate. As an electron beam resist, a material written in "Thin Film Handbook" (Ohmsha, Ltd.) such as PMMA can be used. The resist to be used in this case preferably has a thickness of 10 nm or more and 1 mm or less.

The area of the electrode 23 serving as a working electrode can be made uniform by covering the electrode 23 with a photoresist and performing lithography. With this process, the amounts of ligand such as DNA probe to be immobilized become uniform among the electrodes 23. This makes it possible to perform biological material detection with excellent reproducibility. Conventionally, a resist material is generally removed in the end. If, however, the electrode 23 is used for the detection of a gene immobilized to a DNA probe, the resist material can be used as part of the electrode 23 without being removed. In this case, a material having high water resistance must be used as a resist material.

For the thin insulating film to be formed on the electrodes 23, a material other than photoresist materials can be used. For example, oxides, nitrides, and carbides of Si, Ti, Al, Zn, Pb, Cd, W, Mo, Cr, Ta, Ni, and the like and alloys thereof can be used. After a thin film is formed by sputtering, vapor deposition, CVD, or the like using one of these materials, the film is patterned by photolithography to form exposed electrode portions, thus controlling the area constant.

The driving operation of the driving circuit 26 will be described with reference to FIGS. 16A to 16C, 17A to 17C, 18A to 18C, and 19A to 19C. The driving circuit 26 applies voltages having predetermined polarities to the electrodes 23 to sequentially move a detection target biological material in a sample liquid introduced to the sample liquid receiving portion 21 placed on the central portion on the biological material detection element 5 in the array direction of the electrodes 23.

When a detection target biological material is a gene, a sample liquid which is an aqueous solution of genes is supplied from the sample liquid supply pipe 10 to the sample liquid receiving portion 21 on the biological material detection element 5 via the sample liquid introduction portion 8 and guided onto the electrode 23 via the guide groove 22. The charge polarity of the gene is negative. FIGS. 16A to 16C, 17A to 17C, 18A to 18C, and 19A to 19C show cases wherein driving operation is performed when a detection target biological material is a gene. Each of FIGS. 16A to 16C, 17A to 17C, 18A to 18C, and 19A to 19C shows changes in voltage applied state with respect to the electrodes 23 over time. Assume that the voltage applied state (the polarity of a voltage) changes in the order of the suffixes A, B, and C attached to the respective drawing numbers.

Figure 16A:
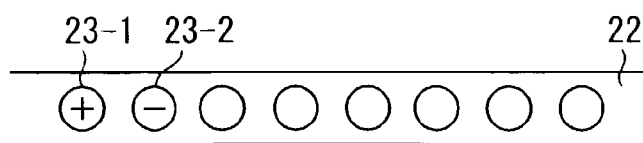
FIGS. 16A to 16C are views showing the first example of the driving operation of the biological material detection element according to the third embodiment.

The examples of driving operation shown in FIGS. 16A to 16C will be described. First of all, as shown in FIG. 16A, a positive voltage whose polarity is opposite to the charge polarity of a gene is applied to an electrode 23-1 nearest to the sample liquid receiving portion 21, and a negative voltage is then applied to an electrode 23-2 adjacent to the electrode 23-1. The sample liquid supplied to the sample liquid receiving portion 21 therefore moves onto the electrode 23-1 owing to the electrostatic attracting force produced by the electrode 23-1 to which the voltage whose polarity is opposite to the charge polarity of the gene is applied. In this case, if a slight negative pressure is applied to the sample liquid, the sample liquid can move more quickly. Since a voltage having an opposite polarity to the charge polarity of the gene is applied to the electrode 23-2 adjacent to the electrode 23-1, the gene is trapped on the electrode 23-1.

Figure 16B:
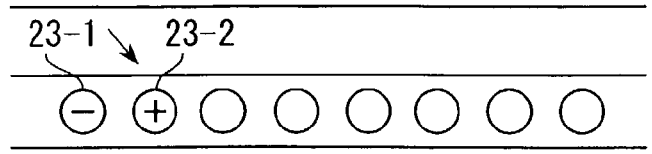

As shown in FIG. 16B, the polarity of the voltage applied to the electrode 23-1 is then inverted to negative polarity, and the polarity of the voltage applied to the adjacent electrode 23-2 is also inverted to positive polarity. At this time, the gene in the sample liquid receives electrostatic repulsive force from the electrode 23-1 to which the voltage having the same polarity as the charge polarity of the gene is applied and electrostatic attracting force from the electrode 23-2 to which the voltage having the opposite polarity to the charge polarity is applied. The gene therefore moves from the electrode 23-1 onto the electrode 23-2 and trapped on the electrode 23-2.

Figure 16C:
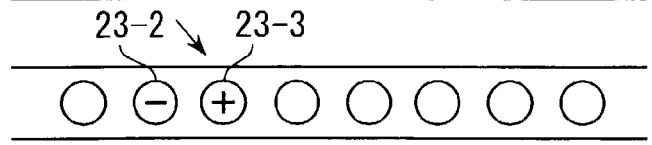

As shown in FIG. 16C, the polarity of the voltage applied to the electrode 23-2 is inverted to negative polarity, and the polarity of the voltage applied to an adjacent electrode 23-3 is also inverted to positive polarity, thereby moving the gene in the sample liquid from the electrode 23-2 onto the electrode 23-3 and trapping it on the electrode 23-3.

Subsequently, the position of an electrode to which a voltage having the same polarity as the charge polarity of the gene in the sample liquid is to be applied and the position of an electrode to which a voltage having an opposite polarity to the charge polarity is to be applied are sequentially shifted in the same manner, thereby sequentially moving the gene onto the adjacent electrodes. In the process of this movement, if the specific gene held on a given electrode has a sequence complementary to that of the ligand immobilized to the electrode, the gene and ligand reach and combine with each other. That is, hybridization occurs.

In this manner, in the biological material detection element 5, the gene sequentially moves on the electrodes 23 along its array direction and is discharged outside the element 5 from the electrode pads 24.

Figure 17A:
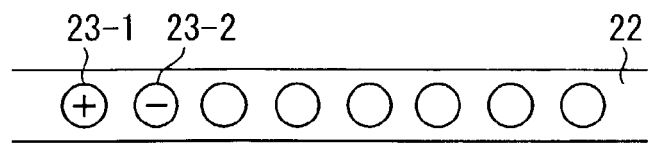
FIGS. 17A to 17C are views showing the second example of the driving operation of the biological material detection element according to the third embodiment.
Figure 17B:
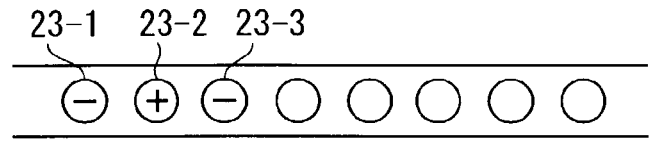
Figure 17C:
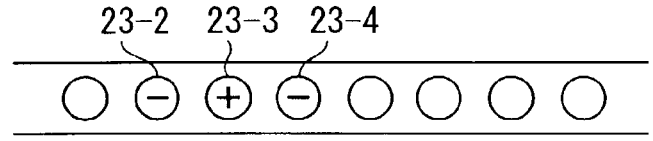

FIGS. 17A to 17C show another example of the driving operation of the driving circuit 26 in this embodiment. Consider the example of driving operation shown in FIGS. 16A to 16C. Referring to FIG. 16B, for example, a positive voltage whose polarity is the same as the charge polarity of the gene is applied to only the electrode 23-1, of the electrodes 23, which is located on the opposite side to the electrode 23-2, on which the gene is trapped, in the moving direction of the gene. As shown in FIG. 17B, however, a positive voltage may also be applied to the electrode 23-3 located along the moving direction of the gene. FIGS. 17A to 17C respectively show voltage applied states at the same timings as those in the case shown in FIGS. 16A to 16C. The first state shown in FIG. 17A is the same as that shown in FIG. 16A. In the case shown in FIGS. 17B and 17C, however, negative voltages are applied to the electrodes located before and after, in the moving direction of the gene, the electrode to which a positive voltage is applied (on the two sides in the array direction of the electrodes 23).

With this operation, since negative voltages are applied to the two electrodes located before and after, in the moving direction of the gene, the gene, of the electrodes 23, on which the gene is trapped and to which a positive voltage is applied, the gene is confined on the electrode on which the gene is trapped by the electrostatic repulsive force produced by the two electrodes, and the gene can be concentrated. This makes it possible to efficiently detect the gene. In addition, the gene need not be amplified or the degree of amplification is relaxed.

Figure 18A:
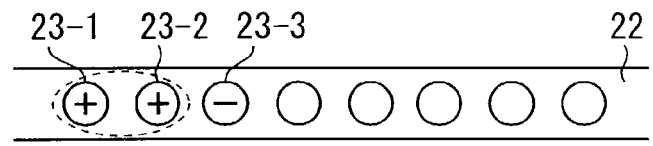
FIGS. 18A to 18C are views showing the third example of the driving operation of the biological material detection element according to the third embodiment.
Figure 18B:
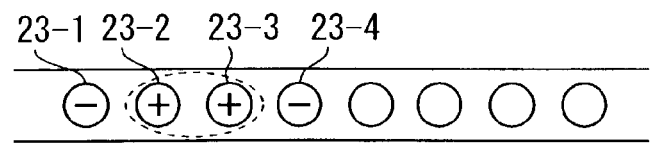
Figure 18C:
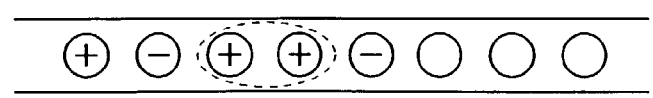

In the example of driving operation shown in FIGS. 18A to 18C, positive voltages are applied to two adjacent electrodes of the electrodes 23, and a voltage having the opposite polarity is applied to an electrode adjacent to the pair of electrodes. This operation is performed while each voltage application position is shifted by one electrode at a time in the array direction of the electrodes 23.

Figure 19A:
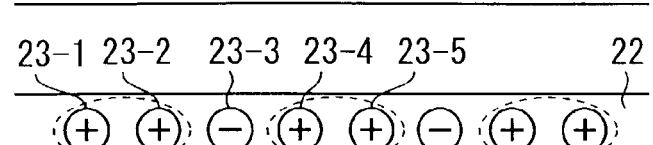
FIGS. 19A to 19C are views showing the fourth example of the driving operation of the biological material detection element according to the third embodiment.
Figure 19B:
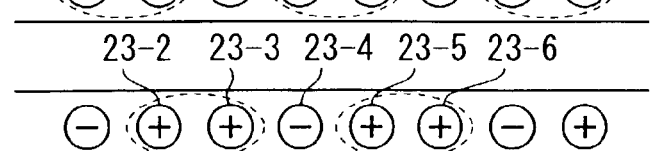
Figure 19C:
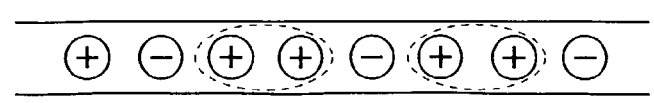

In the example of driving operation shown in FIGS. 19A to 19C, voltages are simultaneously applied to all the electrodes 23. As in the case shown in FIGS. 18A to 18C, positive voltages are applied to two adjacent electrodes of the electrodes 23, and a voltage having the opposite polarity is applied to an electrode adjacent to the pair of electrodes. This operation is performed while each voltage application position is shifted by one electrode at a time in the array direction of the electrodes 23.

Letting n be the number of electrodes, of the electrodes 23, to which positive voltages whose polarity is opposite to the charge polarity of the gene are applied, m be the number of electrodes to which negative voltages whose polarity is the same as the charge polarity are applied, and p be the number of electrodes by which the voltage application positions are shifted when the polarities of applied voltages are switched, n, m, and p can take arbitrary numbers equal to or larger than one. Most simply, it suffices if n m=p=1. In this case, the polarity of an applied voltage is periodically and alternately switched between positive polarity and negative polarity from the viewpoint of one electrode 23.

Figure 20A:
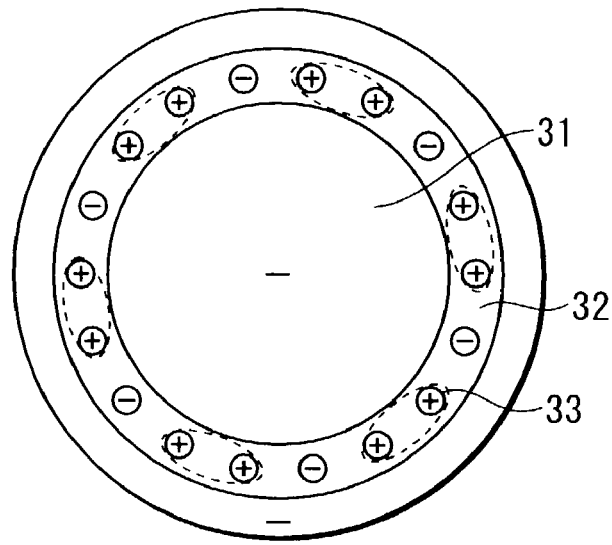
FIGS. 20A to 20C are views for explaining another electrode arrangement of a biological material detection element according to the third embodiment and the concentration and movement of a detection target biological material in the biological material detection element.
Figure 20B:
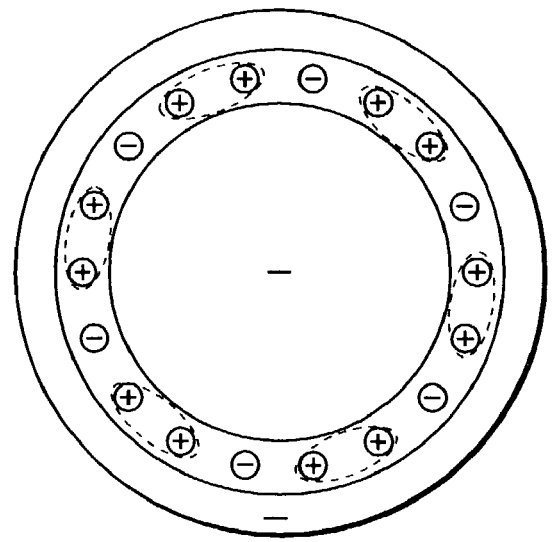
Figure 20C:
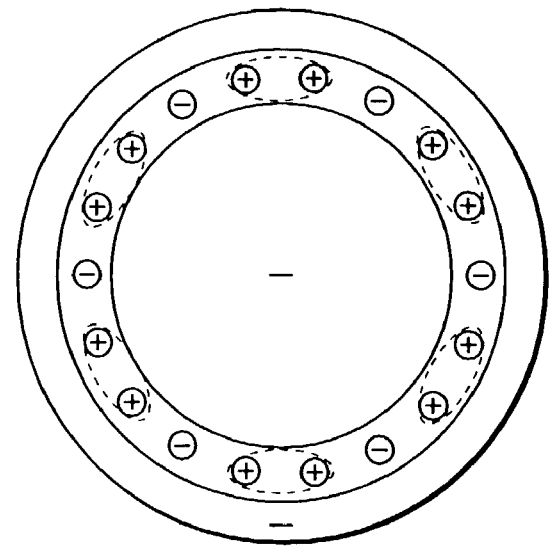

FIGS. 20A to 20C show the electrode arrangement and an example of driving operation of a biological material detection element according to still another embodiment of the present invention. As shown in FIGS. 20A to 20C, according to this embodiment, a guide groove 32 is formed on a circumference centered on a sample liquid receiving portion 31 placed on the central portion of an element substrate in the biological material detection element, and electrodes 33 to which ligands are immobilized are arrayed on the bottom portion of this guide groove 32. A sample liquid supplied to the sample liquid receiving portion 31 is guided into the guide groove 32 and reaches the electrode 33.

In this arrangement, as in the example of driving operation shown in FIGS. 19A to 19C, a detection target biological material, e.g., a gene, in a sample liquid can be moved on the electrodes 33 along the circumference by applying voltages to the electrodes 33 using a driving circuit (not shown) in the manner shown in FIGS. 20A to 20C.

First of all, as shown in FIG. 20A, positive voltages are applied to a pair of adjacent electrodes, of the electrodes 33, which are enclosed with the dotted line, and a negative voltage is applied to an electrode adjacent to this pair of electrodes. After an elapse of a predetermined unit time, as shown in FIG. 20B, the position of the pair of electrodes to which positive voltages are to be applied is shifted by one electrode, and the position of the electrode which is adjacent to the pair of electrodes and to which a negative voltage is to be applied is shifted by one electrode accordingly. When the predetermined unit time has further elapsed, the position of the pair of electrodes to which positive voltages are to be applied and the position of the electrode to which a negative voltage is to be applied are shifted by one electrode, as shown in FIG. 20C. Subsequently, such switching of the polarities of applied voltages will be done every unit time, i.e., in a predetermined cycle. With this operation, a detection target biological material (e.g., a gene) in the sample liquid moves on the array of adjacent electrodes 33 in the circumferential direction. This allows the detection target biological material to uniformly and efficiently react with the ligand immobilized to each electrode 33.

In this manner, the detection target biological material in the sample liquid introduced in the biological material detection element can be sequentially moved on the electrodes 33 while being concentrated. That is, according to this embodiment, since the detection target biological material is concentrated on the electrode 33 to which the ligand is immobilized, there is no need to amplify the detection target biological material by a gene amplification method such as the PCR method as in the prior art, and the detection target biological material and ligand can be made to efficiently reach with each other. This improves the detection efficiency.

Figure 21A:
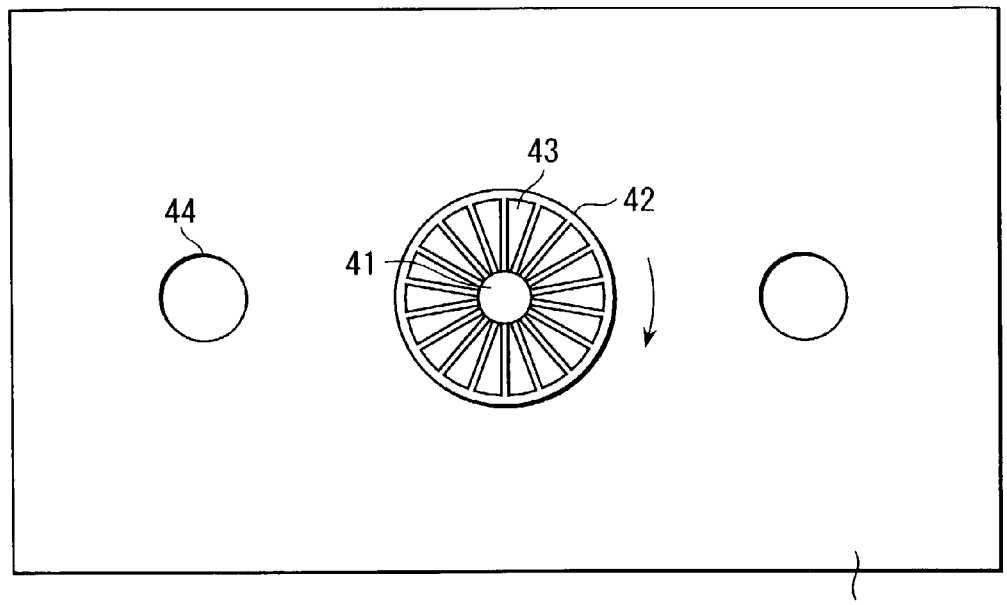
FIGS. 21A and 21B are a plan view and sectional view showing still another arrangement of a biological material detection apparatus according to the third embodiment.
Figure 21B:
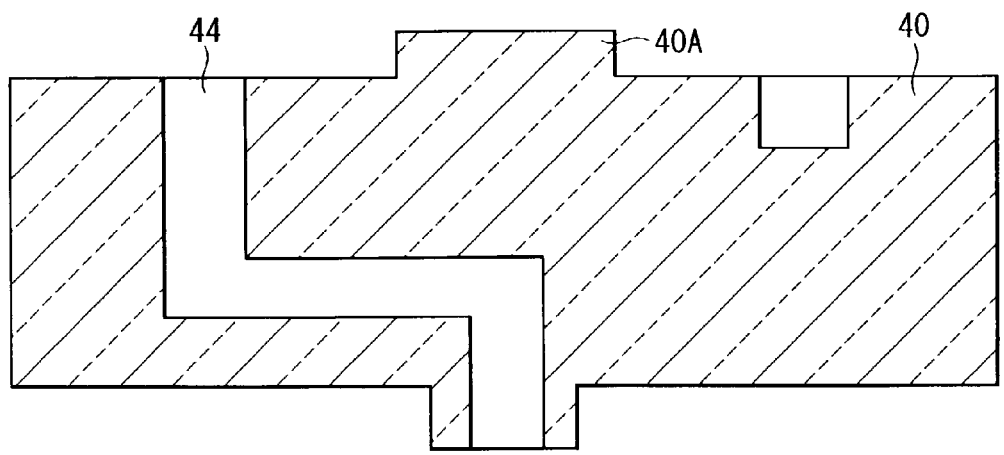

FIGS. 21A and 21B are a plan view and sectional view showing still another arrangement of a biological material detection apparatus according to the third embodiment.

In the biological material detection apparatus according to this embodiment, a sample liquid receiving portion 41 is formed in the center of a protruding portion 40A formed on the central portion of a base 40, and a recess portion 42 is so formed as to be centered on the sample liquid receiving portion 41. In addition, a plurality of fan-shaped electrodes 43 are formed within the recess portion 42 so as to radially extend from the sample liquid receiving portion 41. Ligands are immobilized to the electrodes 43. In addition, the base 40 has a sample liquid passage hole 44 which guides the sample liquid that has passed through the biological material detection element to the sample liquid outlet.

In this biological material detection apparatus as well, by driving the electrodes 43 using a driving circuit (not shown) in the same manner as in the case described with reference to FIGS. 20A to 20C, the detection target biological material is sequentially moved in the circumferential direction in which the electrodes 43 are arrayed while being concentrated, and can be made to efficiently react with the ligand.

Figure 22:
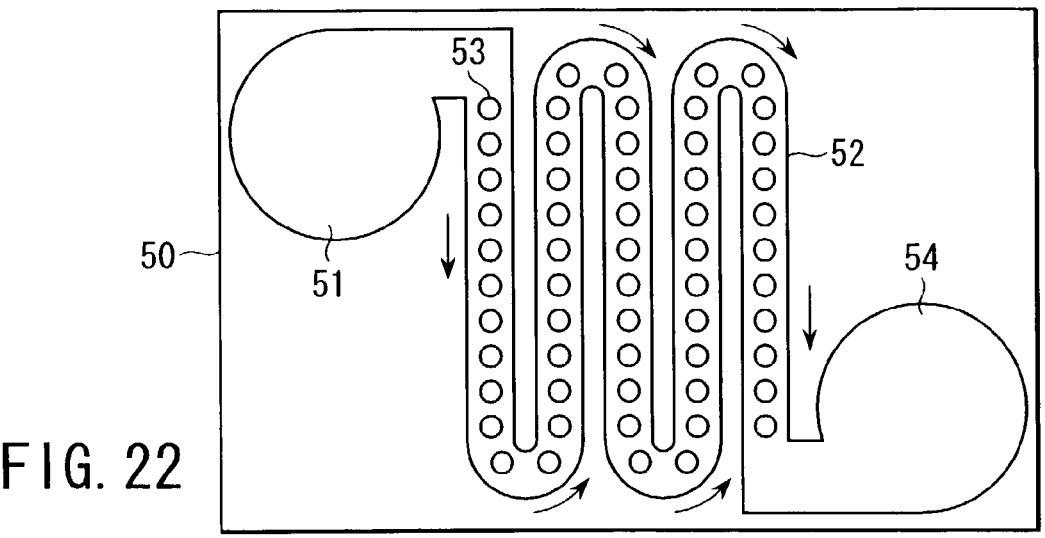
FIG. 22 is a plan view showing the arrangement of a biological material detection element according to a modification of the third embodiment.

FIG. 22 is a plan view showing the arrangement of a biological material detection element according to a modification of the third embodiment.

A sample liquid receiving portion 51 and sample liquid discharge portion 54 are arranged near two opposite corners on an element substrate 50. A zigzag sample liquid guide groove 52 is formed between the sample liquid receiving portion 51 and the sample liquid discharge portion 54. Electrodes 53 to which ligands are immobilized are arranged in this sample liquid guide groove 52.

In the use of the biological material detection element having this arrangement as well, a detection target biological material is sequentially moved in the circumferential direction in which the electrodes 53 are arrayed by performing the same driving operation as that described with reference to FIGS. 16A to 16C, 18A to 18C, 19A to 19C, and 20A to 20C using a driving circuit (not shown). In addition, since the detection target biological material is concentrated during movement, the ligand can be made to efficiency react with the material.

FOURTH EMBODIMENT

Figure 23:
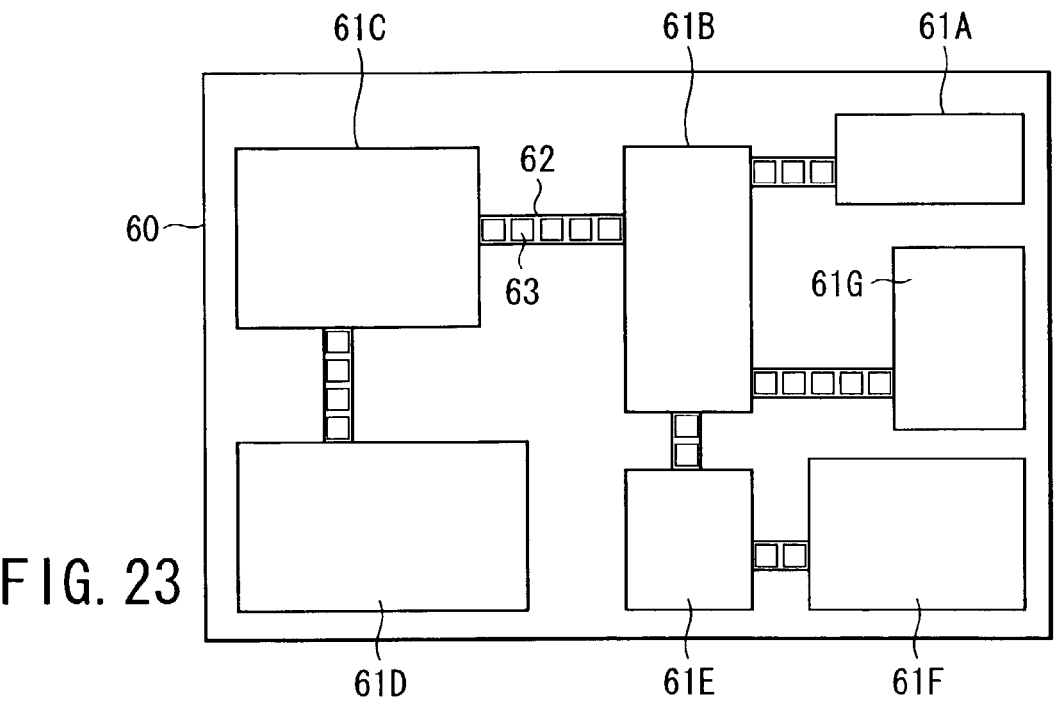
FIG. 23 is a plan view showing the schematic arrangement of a biological material processing apparatus, to which a charged material moving apparatus is applied, according to a fourth embodiment of the present invention.

FIG. 23 shows the schematic arrangement of a biological material processing apparatus having a plurality of reaction steps according to a fourth embodiment of the present invention.

In this embodiment, a plurality of reaction chambers 61A to 61F are arranged on a substrate 60. These reaction chambers 61A to 61F communicate with each other via sample liquid guide grooves 62, as needed. Electrodes 63 are arrayed in the sample liquid guide grooves 62. For example, ligands may be immobilized to the electrodes 63.

In this biological material processing apparatus as well, a detection target biological material is sequentially moved in the circumferential direction in which the electrodes 63 are arrayed by performing the same driving operation as that described with reference to FIGS. 16A to 16C, 18A to 18C, 19A to 19C, and 20A to 20C using a driving circuit (not shown). In addition, since the detection target biological material is concentrated during movement, reactive processing of the detection target biological material can be efficiently done in the reaction chambers 61A to 61F.

FIFTH EMBODIMENT

Figure 24:
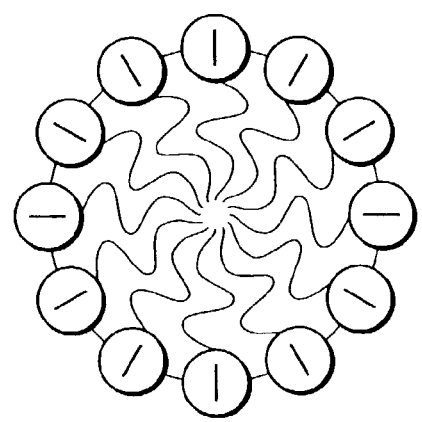
FIG. 24 is a view showing a micellar structure used in a biological material processing apparatus, to which a charged material moving apparatus is applied, according to a fifth embodiment of the present invention.
Figure 25:
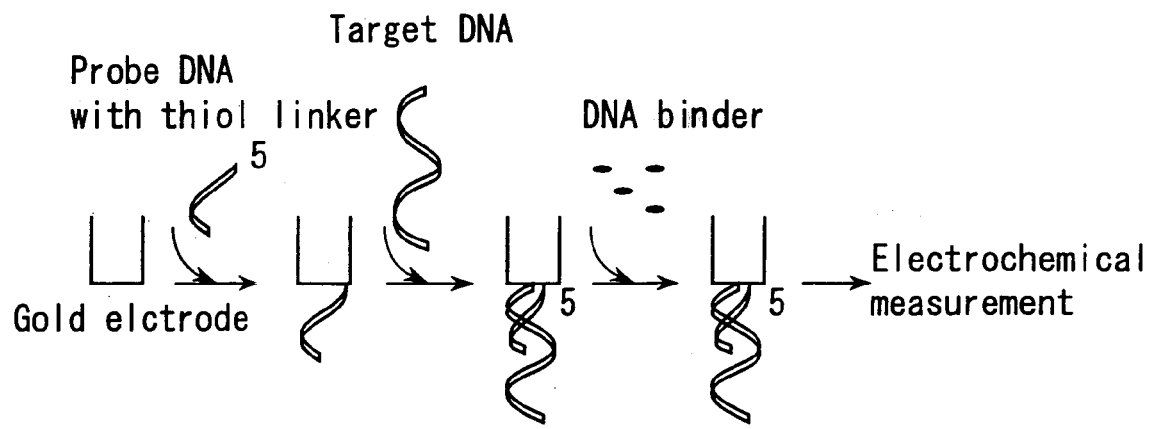
FIG. 25 is a view for explaining the principle of an electrochemical gene detection method.
Figure 26:
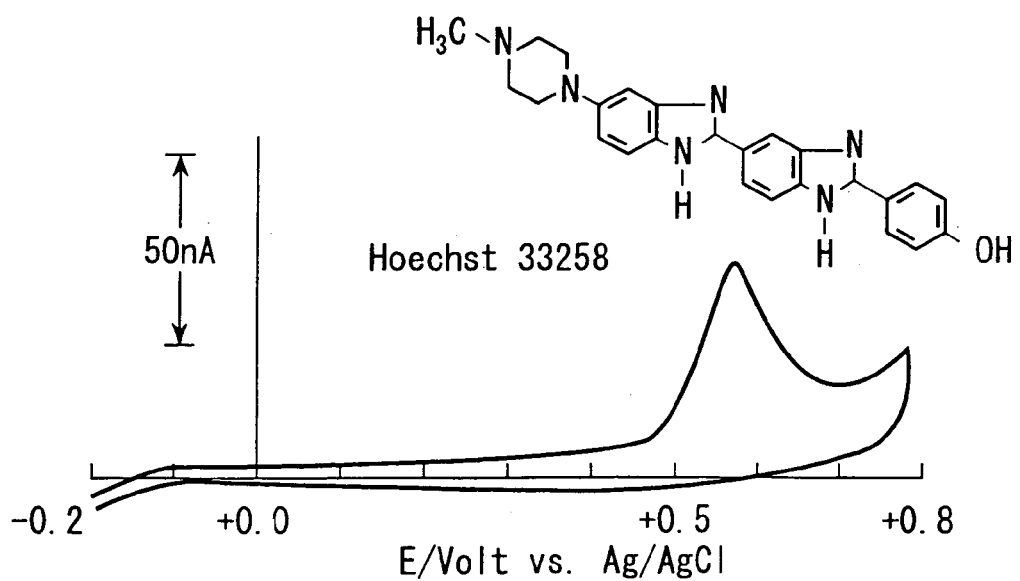
FIG. 26 is a graph showing an example of a current-potential response of a DNA binder (Hoechst 33258) in the electrochemical gene detection method.
Figure 27:
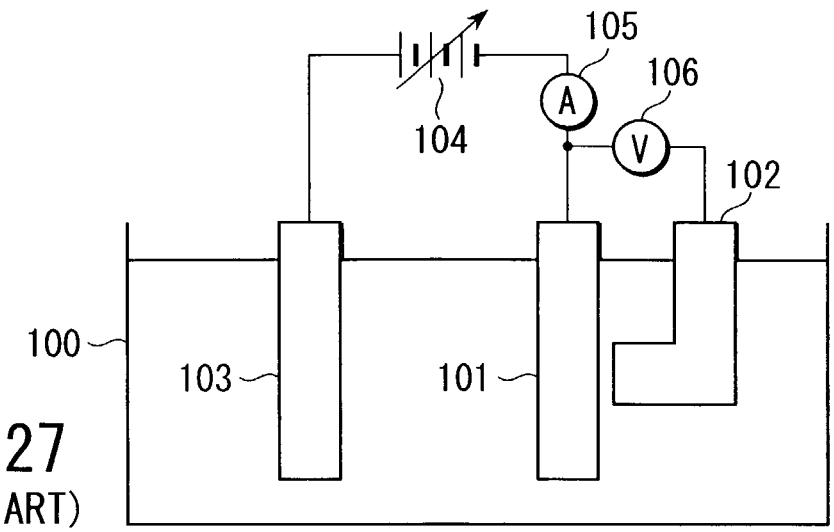
FIG. 27 is a sectional view showing the arrangement of a biological material detection apparatus using conventional electrochemical measurement.
Figure 28:
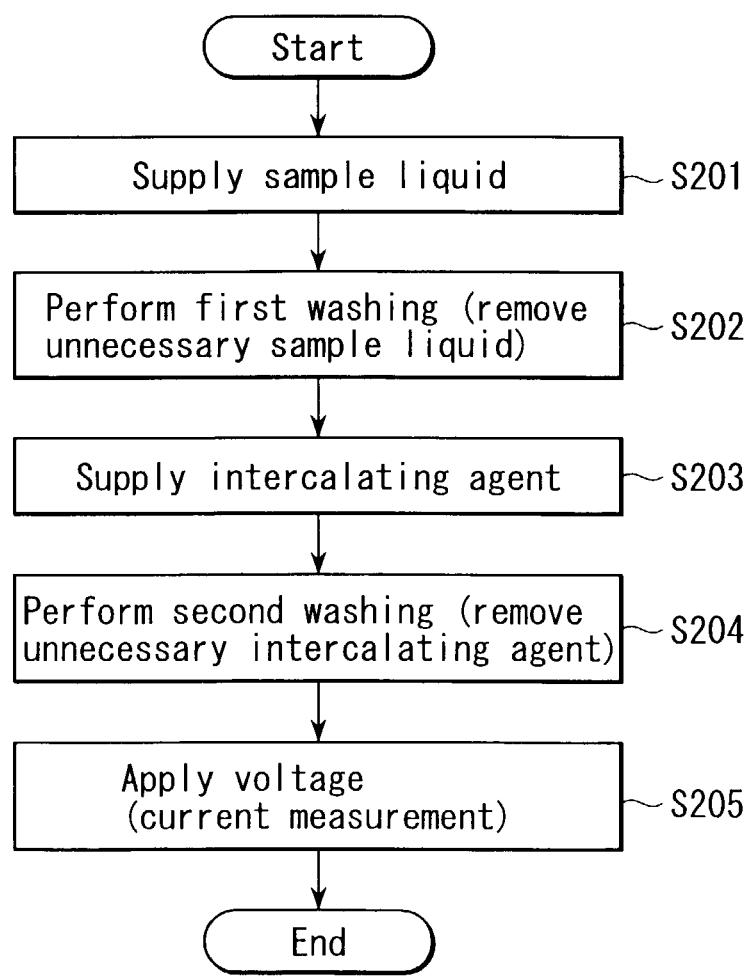
FIG. 28 is a flow chart showing a biological material detection procedure based on conventional electrochemical measurement.
Figure 29:
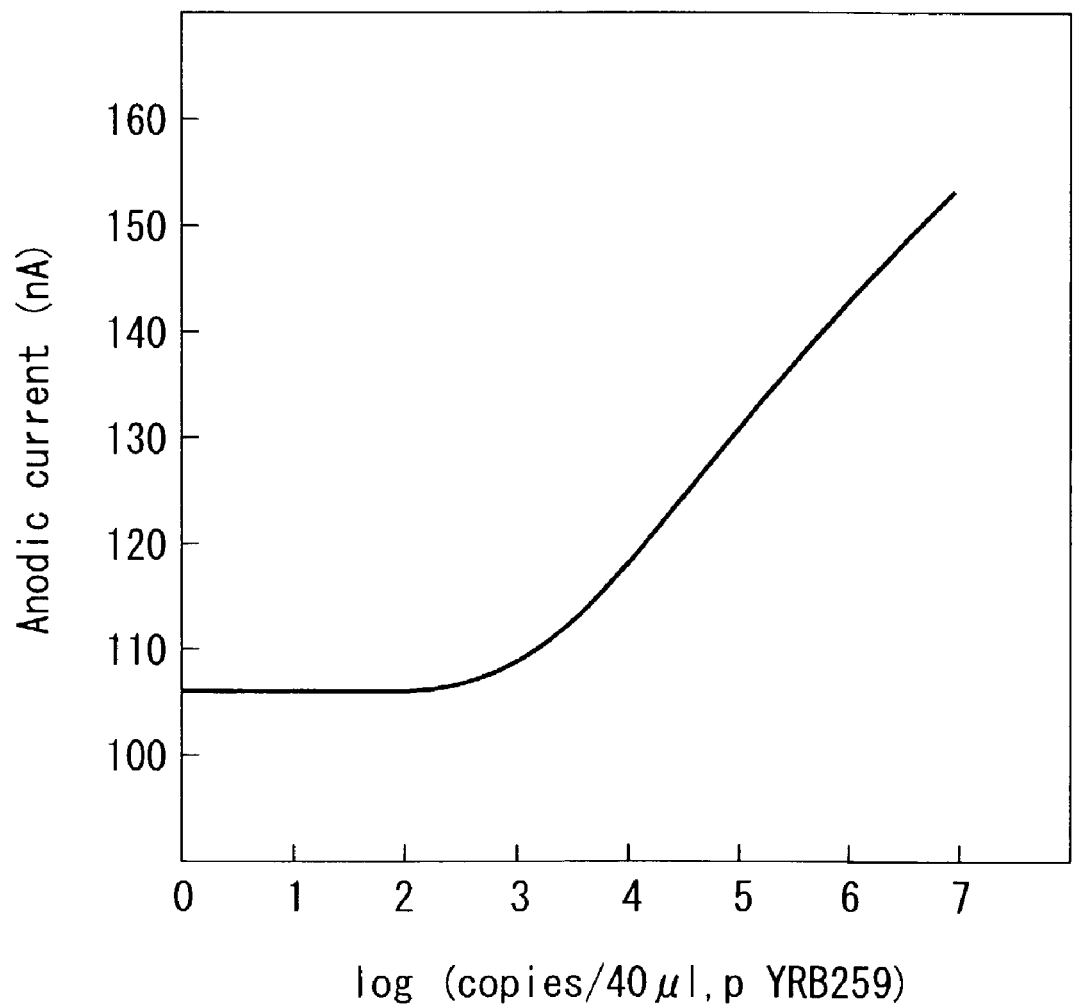
FIG. 29 is a graph showing an example of the gene detection result obtained by biological material detection using conventional electrochemical measurement.

FIG. 24 is a view showing a micellar structure used in a biological material processing apparatus, to which a charged material moving apparatus is applied, according to a fifth embodiment of the present invention. This embodiment is an apparatus used to process a biological material having no charge. In this apparatus, a micellar structure is formed by using, for example, a surfactant.

A micellar structure is a structure in which an uncharged material is covered with a micelle to be forcibly charged. Referring to FIG. 24, a biological material is charged to negative polarity. Even when a biological material forcibly charged by a micellar structure in this manner is to be moved, the biological material moving apparatus or biological material processing apparatus having the arrangement described in each of the above embodiments can be used.

A sample to be processed by the biological material detection element or biological material detection apparatus using the biological material moving apparatus according to the embodiment is, but is not limited to, for example, blood, blood serum, leukocyte, urine, stool, sperm, saliva, tissue, cultured cell, expectoration, and the like. If, a detection target biological material is a gene, the gene is extracted from these samples. The extraction method may be, but is not limited to a liquid-liquid extraction method such as a phenol-chloroform method or a solid liquid extraction method using a carrier. Alternatively, a commercially available nucleic acid extraction method such as QIAamp (available from QIAGEN), SUMAI test (available from Sumitomo Metal Industries, Ltd.) can be used.

The gene sample solution extracted in this manner is then introduced onto the biological material detection element (DNA chip) described in the above embodiment, and a hybridization reaction is caused on an electrode to which a DNA probe as a ligand is immobilized. A buffering solution that falls within the range of ion intensities of 0.01 to 5 and the range of pH5 to pH10 is used as a reaction solution. A hybridization accelerating agent such as dextran sulfate, salmon sperm DNA, bovine thymus DNA, EDTA, or surfactant can be added to this solution, as needed. The extracted sample gene is added to this solution. The solution must be heat-denatured at 90° C. or more before introduction into the biological material detection element. An unreacted sample gene can be recovered from the sample liquid outlet 4 to be introduced into the biological material detection element again, as needed.

The extracted gene can be detected by marking in advance it with a fluorescent dye such as FITC, Cy3, Cy5, or rhodamine, an enzyme such as biotin, hapten, oxidase, or phosphatase, or an electrochemically active material such as ferrocene or quinones, or by using a second probe marked with such a material. If the gene is marked with a fluorescent dye, it can be optically detected.

When the gene is to be detected by using an electrochemically active DNA binder, detection is done by the following procedure.

A DNA binder which selectively combines with a double stranded DNA portion is made to react with the double stranded DNA portion formed on the surface of an electrode (working electrode) to which a DNA probe is immobilized, thereby performing electrochemical measurement. The DNA binder to be used in this case is, but is not limited to, for example, Hoechst 33258, acridine orange, quinaccrine, downomycin, metallointercalator, bis-intercalator such as bis-acridine, tris-intercalator, or polyintercalator. In addition, such an intercalator can be modified in advance by an electrochemically active metal complex such as ferrocene or viologen.

Although the concentration of a DNA binder varies depending on the type of material, the material is generally used within the range of 1 ng/mL to 1 mg/mL. In this case, a buffering agent within the range of ion intensities of 0.001 to 5 and the range of pH5 to pH10 is used.

After an electrode serving as a working electrode and a DNA binder are made to react with each other, cleaning is performed, and electrochemical measurement is performed. Electrochemical measurement is performed by a triple electrode type including a reference electrode, counterelectrode, and working electrode or a double electrode type including a counterelectrode and working electrode. In measurement, a potential equal to or higher than a potential at which the DNA binder reacts is applied, and a reaction current value originating from the DNA binder is measured. In this case, the potential is swept at a constant velocity or pulses or a constant potential can be applied. In measurement, currents and voltages are controlled by using a potentiostat, digital multimeter, function generator, and the like.

EXAMPLE 4

The biological material detection element described with reference to FIGS. 19A to 19C was formed into an interferon curative effect predicting DNA chip and the following experiment was conducted.

First of all, a chromosome DNA was extracted from human leukocyte, a MxA gene fragment of about 100 bp was PCR-amplified by using a proper primer. The amplified fragment was heat-denatured. The resultant fragment was then introduced into the DNA chip. Note that a DNA probe associated with SNP (single nucleotide polymorphism) existing in the MxA gene was immobilized in advance on an electrode 23 of the DNA chip. After the sample was introduced, the electrodes 23 were driven. After an excess sample liquid was finally observed, cleaning was done with a buffering agent. When a DNA binder (Hoechst 33258) was made to act, it was found that an interferon curative effect could be predicted.

In this case, it was found that when the introduced gene was moved to the peripheral portion while being concentrated by switching the polarities of voltages applied to the electrodes 23 in the same manner as described with reference to FIGS. 19A to 19C, and the gene was moved on the array of electrodes 32 by switching the polarities of voltages applied to the respective electrodes 23 while the gene was trapped on the electrode 23, a curative effect could be accurately predicted without performing PCR amplification.

EXAMPLE 5

The biological material detection element described with reference to FIG. 22 was formed into a tumor marker detection chip, and the following experiment was conducted.

To form a tumor marker detection chip, antibodies for various human tumor markers are immobilized to the surfaces of electrodes 53. In order to prevent nonspecific adsorption, 1% bovine serum albumin was made to act. When the charges of the electrodes were changed by operation similar to that in Example 1, and tumor markers were detected by using the human serum as a sample, it was found that the markers could be detected with high reproducibility and high sensitivity on the order of 0.1 ng/mL. In this case, an antibody marked with horseradish peroxidase was used as the second antibody, and a framework for luminescence detection was supplied lastly.

The above embodiment has exemplified only the biological material moving apparatus. However, the present invention is not limited to the biological material moving apparatus and can be applied to all apparatuses for moving charged materials having predetermined charge polarities.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biological material detection apparatus which detects a charged biological material contained in a sample liquid, comprising:
   a biological material detection element having a substrate and a plurality of electrodes which are arrayed at predetermined intervals along a circumferential direction on the substrate and to which ligands that react with predetermined biological materials are respectively immobilized;
   a sample liquid introduction part to introduce the sample liquid to a central portion of the array of the electrodes on the substrate;
   a sample liquid moving mechanism to move the sample liquid introduced to the central portion on the substrate by the sample liquid introduction part radially toward the electrodes by an electrostatic attracting force produced by the electrodes; and
   a control device configured to control a process which is performed repeatedly, the process including
   (a) supplying an intercalating agent onto the biological material detection element,
   (b) measuring an electrochemical signal from the intercalating agent which is based on a reaction between the charged biological material and the ligand, and
   (c) removing the intercalating agent adhering to the ligand.

2. A biological material detection apparatus to which a sample liquid containing a charged biological material is introduced, and which detects the biological material, comprising:
   a biological material detection element having a substrate, at least one first electrode placed at a position on the substrate to which the sample liquid is introduced, and a plurality of second electrodes which are arrayed at predetermined intervals around the first electrode on the substrate along a circumferential direction, and to which ligands that react with predetermined biological materials are respectively immobilized;
   a driving circuit which drives the biological material detection element by performing a driving operation of applying a voltage having the same polarity as a charge polarity of the biological material to the first electrode, and applying a voltage having an opposite polarity to the charge polarity to at least some of the second electrodes, the first electrode and the second electrode each producing an electrostatic field by which the charged biological material is moved toward the second electrodes; and
   a control device configured to control a process which is performed repeatedly, the process including
   (a) supplying an intercalating agent onto the biological material detection element,
   (b) measuring an electrochemical signal from the intercalating agent which is based on a reaction between the charged biological material and the ligand, and
   (c) removing the intercalating agent adhering to the ligand.

3. The apparatus according to claim 2, wherein the driving circuit further performs a driving operation of applying a voltage having an opposite polarity to the charge polarity to some of the second electrodes in the circumferential direction and applying a voltage having the same polarity as the charge polarity to some other electrodes of the second electrodes, while sequentially changing positions of electrodes to which voltages having the opposite polarity and same polarity are to be applied.

4. The apparatus according to claim 2, wherein the biological material detection element further includes at least two annular electrodes concentrically arranged between the first electrode and the array of the second electrodes.

* * * * *